(12) United States Patent
Shia et al.

(10) Patent No.: US 8,354,442 B2
(45) Date of Patent: Jan. 15, 2013

(54) IMIDAZOL-4-ONE AND IMIDAZOLE-4-THIONE COMPOUNDS

(75) Inventors: Kak-Shan Shia, Taipei (TW);
Chien-Huang Wu, Taipei County (TW);
Teng-Kuang Yeh, Bellevue, WA (US);
Yu-Sheng Chao, Monmouth Junction, NJ (US)

(73) Assignee: National Health Research Institutes, Miaoli County (TW)

( * ) Notice: Subject to any disclaimer, the term of this patent is extended or adjusted under 35 U.S.C. 154(b) by 313 days.

(21) Appl. No.: 12/609,630

(22) Filed: Oct. 30, 2009

(65) Prior Publication Data

US 2010/0113546 A1 May 6, 2010

Related U.S. Application Data

(60) Provisional application No. 61/110,627, filed on Nov. 3, 2008.

(51) Int. Cl.
*A61K 31/4178* (2006.01)
*C07D 403/02* (2006.01)

(52) U.S. Cl. .................................... 514/386; 548/312.4

(58) Field of Classification Search ........................ None
See application file for complete search history.

(56) References Cited

U.S. PATENT DOCUMENTS

| 5,624,941 A | 4/1997 | Barth et al. |
| 6,620,804 B2 | 9/2003 | Chang et al. |
| 6,958,339 B2 | 10/2005 | Kubota et al. |
| 2001/0011090 A1 | 8/2001 | Kubota et al. |
| 2005/0261281 A1 | 11/2005 | Lazzari et al. |
| 2008/0021031 A1 | 1/2008 | Shia et al. |

FOREIGN PATENT DOCUMENTS

| EP | 1623741 | 2/2006 |
| JP | 02-053787 | 2/1990 |
| JP | 2053787 | 2/1990 |
| WO | WO 2007-124854 | 11/2007 |

OTHER PUBLICATIONS

Wu et al. "Discovery of 2-[5-(4-Chloro-phenyl)-1-(2,4-dichloro-phenyl)-4-ethyl-1*H*-pyrazol-3yl]-1,5,5-trimethyl-1,5-dihydro-imidazol-5-thione (BPR-890) via an Active Metabolite. A Novel, Potent and Selective Cannabinoid-1 Receptor Inverse Agonist with High Antibesity Efficacy in DIO Mice." Journal of Medicinal Chemistry, Jun. 16, 2009, vol. 52, pp. 4496-4510.

Jeon et al. "The Synthesis of a New Pyrazolyimidazolinone via 1,3-Dipolar Cycloaddition Reaction of *N*-Methyl Sydnone with Methyl Propiolate." Bulletin of the Korean Chemical Society, Mar. 21, 1998, vol. 19, No. 7, pp. 725-726.

International Search Report and Written Opinion for International Application No. PCT/US2009/062771, dated Jul. 8, 2010, 12 pages.

Clark et al., "Decreased Incidence of Prostate Cancer with Selenium Supplementation: Results of a Double-Blind Cancer Prevention Trial," *British Journal of Urology*, 81:730-734 (1998).

Clark et al., "Effects of Selenium Supplementation for Cancer Prevention in Patients with Carcinoma of the Skin," JAMA, 276:1957-1963 (1996).

Diwadkar-Navsariwala et al., "Selenoprotein Deficiency Accelerates Prostate Carcingenesis in a Transgenic Model," *PNAS*, 103(21):8179-8184 (2006).

Database CAS Online on STN, Chem. Abst., Accession No. 2005:1242633, US 20050261281 Al (Lazzari et al.) Nov. 24, 2005; abstract.

Finar, "Preparation and Properties of Some Bipyrazolyls," Journal of thr Chemica Society, 1956 pp. 12288 (Abstract).

Morimoto et al., caplus an 1970:456092.

Tseng et al., "Bioisosteric Replacement of the Pyrazile 5-Aryl Moiety of N-(Piperidin-l-yl)-5-(4-chlorophenyl)-1-(2,4-dichlorophenyl)-4-methyl-1H-pyrazole-3-caroxamide (SR141716A). A Novel Series of Alkynylthiophenes as Potent and Selective Cannabinoid-1 Receptor Antagonists," J. Med. Chem., 51:5397-5412 (2008).

Obata et al., caplus an, 1994:700884.

*Primary Examiner* — Kamal Saeed
(74) *Attorney, Agent, or Firm* — Occhiuti Rohlicek & Tsao LLP

(57) ABSTRACT

Imidazol-4-one or imidazole-4-thione compounds of formula (I):

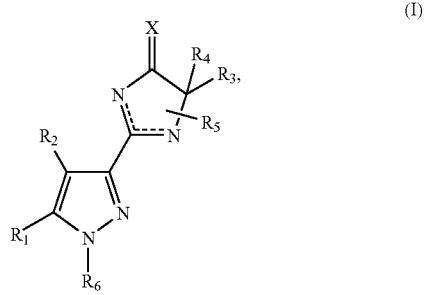

wherein X, $R_1$, $R_2$, $R_3$, $R_4$, $R_5$, and $R_6$ are defined herein. Also disclosed is a method for treating a cannabinoid receptor-mediated disorder with these compounds.

31 Claims, No Drawings

IMIDAZOL-4-ONE AND IMIDAZOLE-4-THIONE COMPOUNDS

CROSS-REFERENCE TO RELATED APPLICATION

This application claims the benefit of the priority pursuant to 35 U.S.C. §119(e) of U.S. Provisional Patent Application No. 61/110,627, filed Nov. 3, 2008. The content of the prior application is incorporated herein by its entirety.

BACKGROUND

Cannabinoids isolated from Cannabis sativa have been recognized for centuries as therapeutic agents. For example, they have been utilized for analgesia, muscle relaxation, appetite stimulation, and anti-convulsion. Recent studies also indicate their potential therapeutic effects in treating cancer and alleviating the symptoms of chronic inflammatory diseases, such as rheumatism and multiple sclerosis.

The actions of cannabinoids are mediated by at least two types of cannabinoid receptors, CB1 and CB2 receptors, both of which belong to the G-protein-coupled receptor (GPCR) superfamily. The CB1 receptor is predominantly expressed in the brain to mediate inhibition of transmitter release and the CB2 receptor is primarily expressed in immune cells to modulate immune response. See Matsuda et al., Nature (1990) 346:561 and Munro et al., Nature (1993) 365:61.

Compared to other GPCRs, the CB1 receptor is typically expressed at higher levels. In the central nervous system, it is highly expressed in the cerebral cortex, hippocampus, basal ganglia, and the cerebellum, but has relatively low levels in the hypothalamus and the spinal cord. See, e.g., Howlett et al., Pharmacol Rev (2002) 54:161. Its functions affect many neurological and psychological phenomena, such as mood, appetite, emesis control, memory, spatial coordination of muscle tone, and analgesia. See, e.g., Goutopoulos et al., Pharmacol Ther (2002) 95:103. In addition to the central nervous system, the CB1 receptor is also present in several peripheral organs, such as the gut, heart, lungs, uterus, ovary, testis, and tonsils. See, e.g., Galiègue et al., Eur J Biochem (1995) 232:54.

The CB2 receptor is 44% identical to the CB1 receptor with a 68% identity in the trans-membrane regions. See Munro et al., Nature (1993) 365:61. Compared to the CB1 receptor, the CB2 receptor has a more limited distribution with a high expression in the spleen and tonsils, and a low expression in the lungs, uterus, pancreas, bone marrow, and thymus. Among immune cells, B cells express the CB2 receptor at the highest level, followed in order by natural killer cells, monocytes, polymorphonuclear neutrophils, and T lymphocytes. See Galiègue et al., Eur J Biochem (1995) 232:54. Activation of CB2 receptors has been shown to have analgesic effects in inflammatory models involved in neurodegeneration diseases (such as Alzheimer's disease), and play a role in the maintenance of bone density and progression of atherosclerotic lesions. See, e.g., Malan et al., Pain (2001) 93:239; Benito et al., J Neurosci (2003) 23:11136; Ibrahim et al., Proc Natl Acad Sci USA (2003) 100:10529; Idris et al., Nat Med (2005) 11:774; and Steffens et al., Nature (2005) 434:782.

SUMMARY

This invention is based on the unexpected discovery that certain imidazol-4-one or imidazole-4-thione compounds are effective in treating cannabinoid receptor-mediated disorders.

In one aspect, this invention relates to a compound of formula (I):

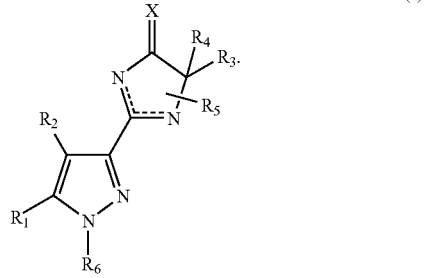

In formula (I), one of the two ----- bonds is a single bond and the other is a double bond; X is O or S; and each of $R_1$, $R_2$, $R_3$, $R_4$, $R_5$, and $R_6$, independently, is H, halo, alkyl, alkenyl, alkynyl, aryl, heteroaryl, cycloalkyl, cycloalkenyl, heterocycloalkyl, or heterocycloalkenyl, or $R_3$ and $R_4$, together with the carbon atom to which they are bonded, are cycloalkyl, cycloalkenyl, heterocycloalkyl, heterocycloalkenyl, aryl, or heteroaryl.

One subset of the above-described compounds includes those in which X is O. In these compounds, $R_1$ can be aryl or heteroaryl (e.g., phenyl or thiophenyl); each of $R_2$, $R_3$, $R_4$, and $R_5$, independently, can be H or alkyl; or $R_6$ can be aryl or heteroaryl (e.g., phenyl substituted with halo).

Another subset of the compounds includes those in which X is S. In these compounds, $R_1$ can be aryl or heteroaryl (e.g., phenyl or thiophenyl); each of $R_2$, $R_3$, $R_4$, and $R_5$, independently, can be H or alkyl; or $R_6$ can be aryl or heteroaryl (e.g., phenyl substituted with halo).

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, and allyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl.

The term "cycloalkyl" refers to a monovalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a monovalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, aryl, and heteroaryl mentioned above include both substituted and unsubstituted moieties. Possible substituents on cycloalkyl, heterocycloalkyl, cycloalkenyl, heterocycloalkenyl, aryl, and heteroaryl include, but are not limited to, $C_1$-$C_{10}$ alkyl (e.g., trifluoromethyl), $C_2$-$C_{10}$ alkenyl, $C_2$-$C_{16}$ alkynyl (e.g., arylalkynyl), $C_3$-$C_{20}$ cycloalkyl, $C_3$-$C_{20}$ cycloalkenyl, heterocycloalkyl, $C_1$-$C_{20}$ heterocycloalkenyl, $C_1$-$C_{10}$ alkoxy, aryl (e.g., haloaryl or aryl substituted with halo), aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The imidazol-4-one or imidazole-4-thione compounds described above include the compounds themselves, as well as their salts, their solvates, and their prodrugs, if applicable. A salt, for example, can be formed between an anion and a positively charged group (e.g., amino) on an imidazol-4-one or imidazole-4-thione compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on an imidazol-4-one or imidazole-4-thione compound. Suitable cations include sodium ion, potassium ion, magnesium ion, calcium ion, and an ammonium cation such as tetramethylammonium ion. The imidazol-4-one or imidazole-4-thione compounds also include those salts containing quaternary nitrogen atoms. Examples of prodrugs include esters and other pharmaceutically acceptable derivatives, which, upon administration to a subject, are capable of providing active imidazol-4-one or imidazole-4-thione compounds.

In another aspect, this invention relates to a method for treating a cannabinoid receptor-mediated disorder. The method includes administering to a subject in need thereof an effective amount of one or more imidazol-4-one or imidazole-4-thione compounds of formula (I) shown above. Examples of cannabinoid receptor-mediated disorders include liver fibrosis, hair loss, obesity, metabolic syndrome (e.g., syndrome X), hyperlipidemia, type II diabetes, atherosclerosis, substance addiction (e.g., alcohol addiction or nicotine addiction), depression, motivational deficiency syndrome, learning or memory dysfunction, haemorrhagic shock, ischemia, liver cirrhosis, neuropathic pain, emesis, high intraocular pressure, bronchodilation, osteoporosis, cancer (e.g., prostate cancer, lung cancer, breast cancer, or head and neck cancer), a neurodegenerative disease (e.g., Alzheimer's disease or Parkinson's disease), or an inflammatory disease.

Also within the scope of this invention is a pharmaceutical composition containing one or more of the above-described imidazol-4-one or imidazole-4-thione compounds for use in treating a cannabinoid receptor-mediated disorder, as well as this therapeutic use and use of the compounds for the manufacture of a medicament for treating a cannabinoid receptor-mediated disorder.

The details of one or more embodiments of the invention are set forth in the description below. Other features, objects, and advantages of the invention will be apparent from the description and from the claims.

DETAILED DESCRIPTION

Shown below are exemplary compounds of this invention:

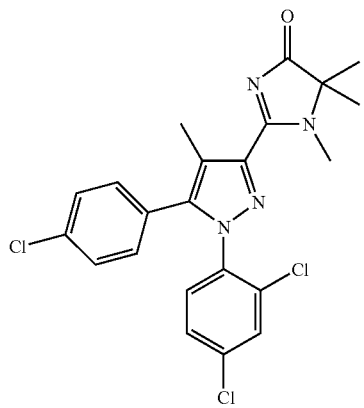

6

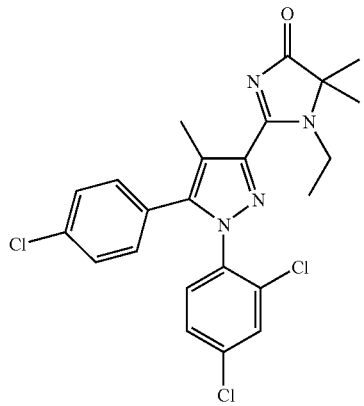

7

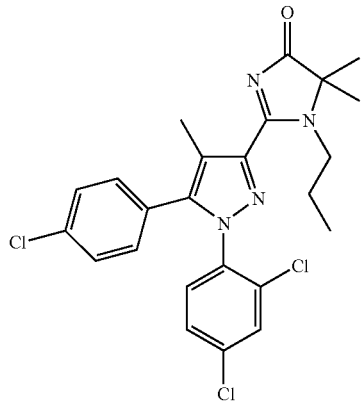

8

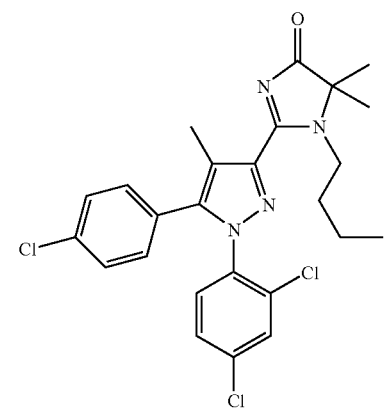
9
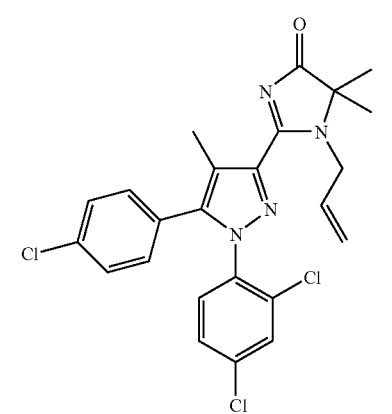
10
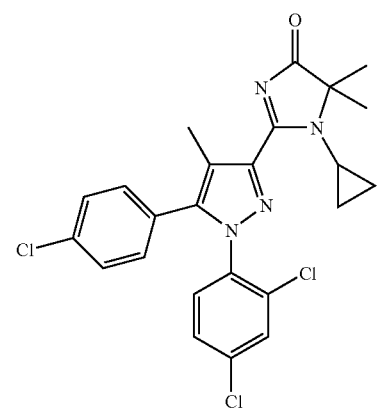
11
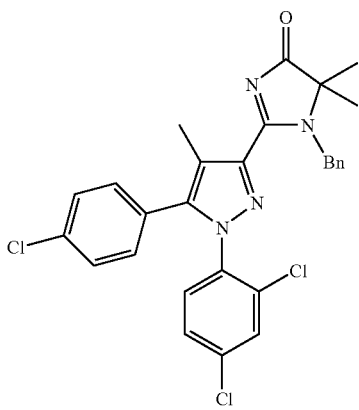
13
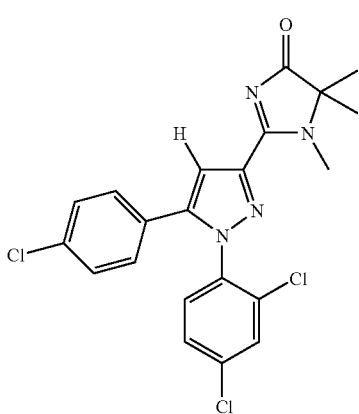
14
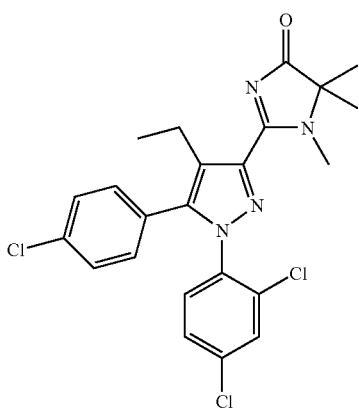
15
12
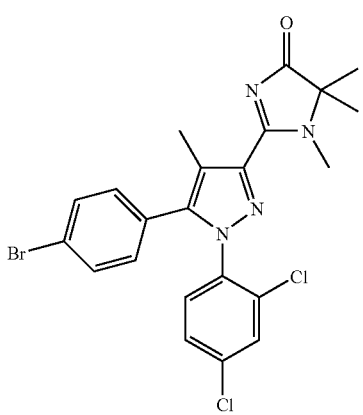
16

17
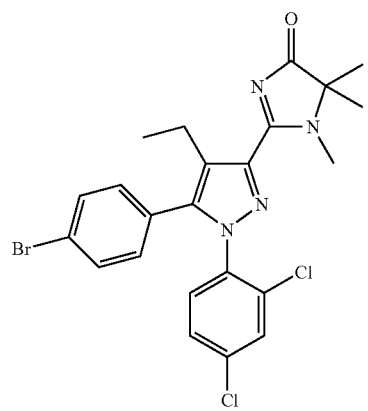
18
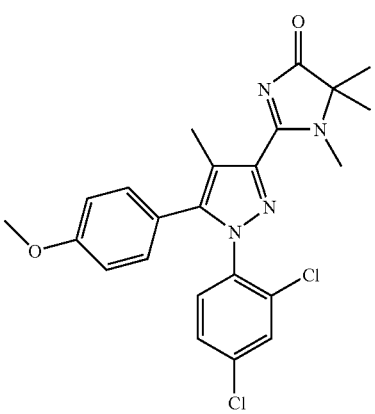
19
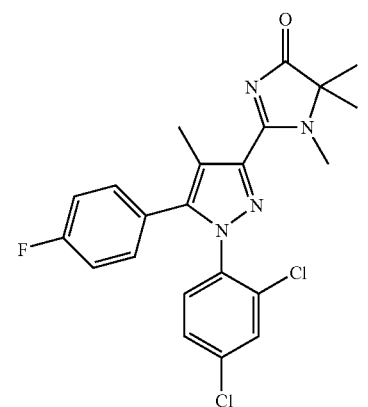
20
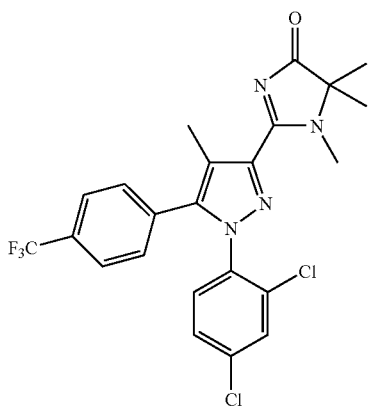
21
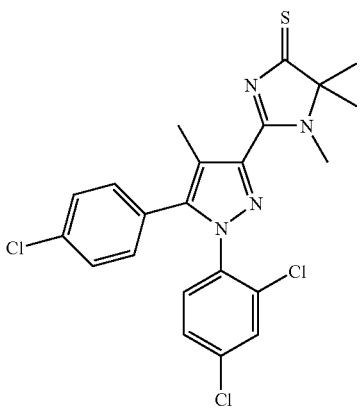
22
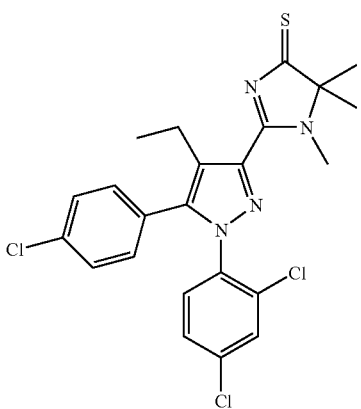
23
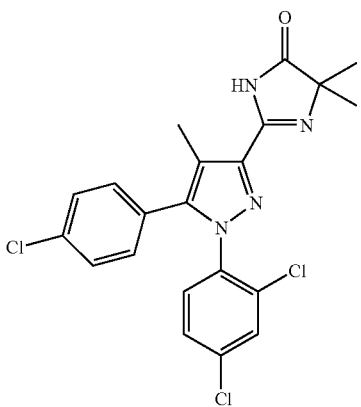
24
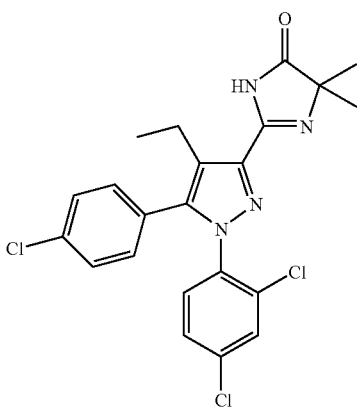

25
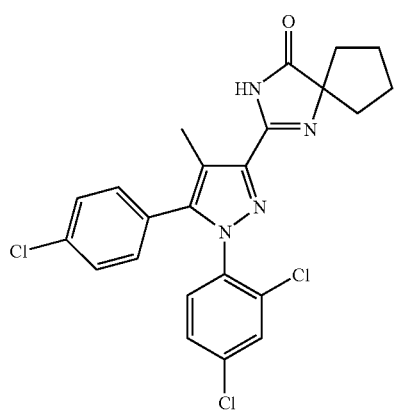
26
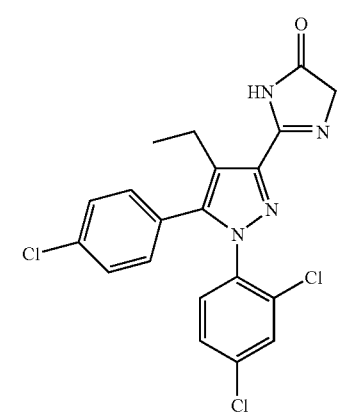
27
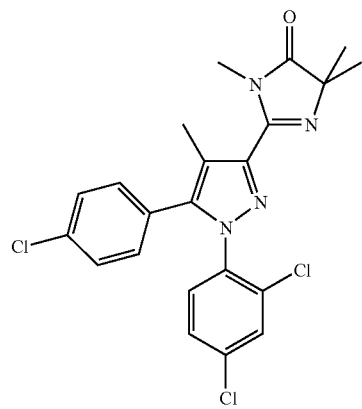
28
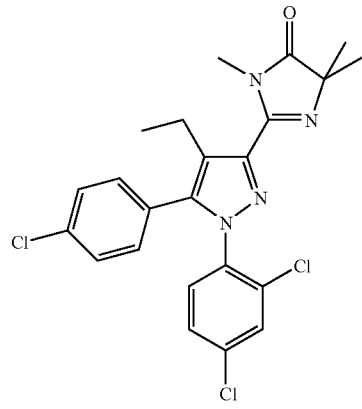
29
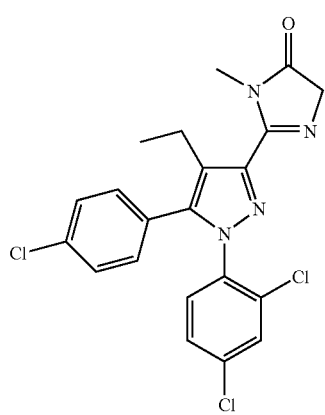
30
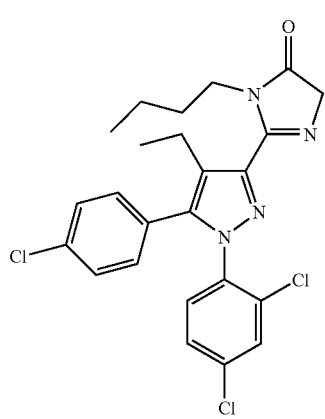
33
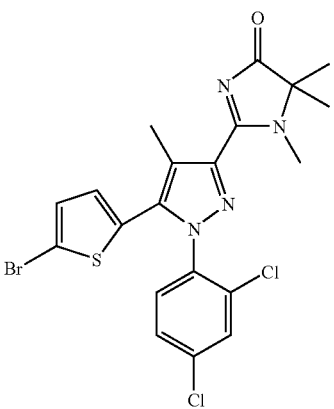
34
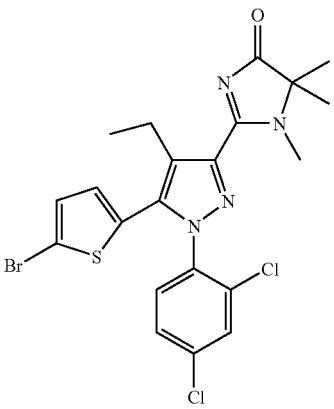

35
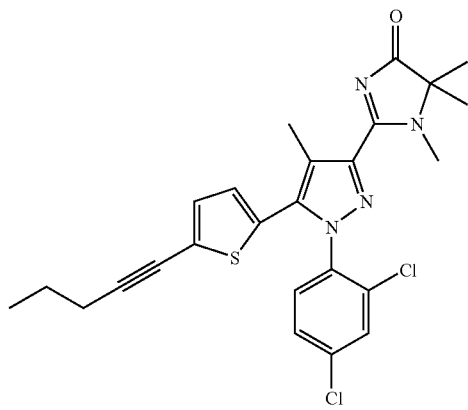
36
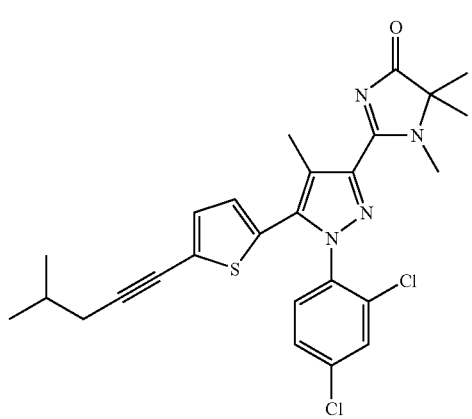
37
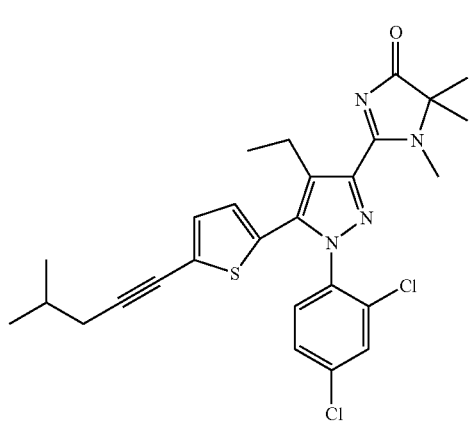
38
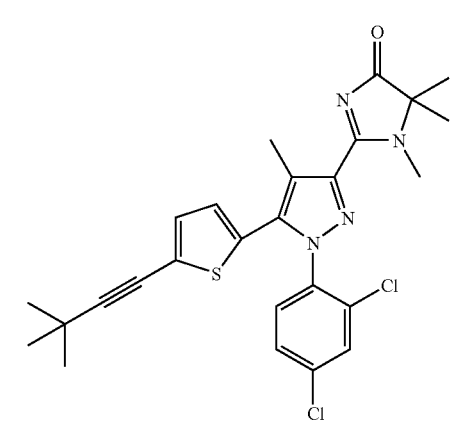
39
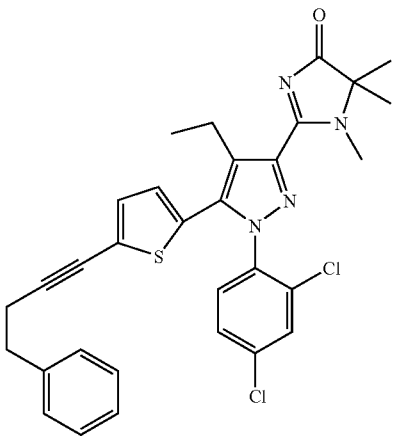
40
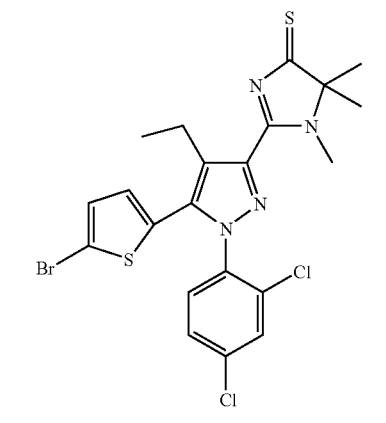
41
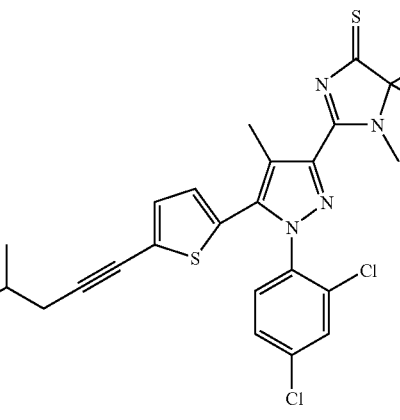
42
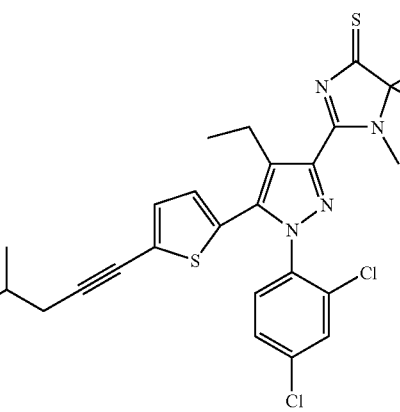

43
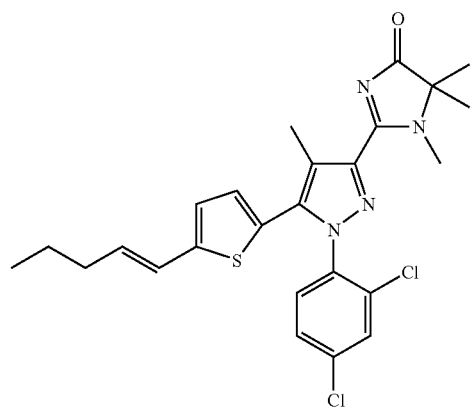
44
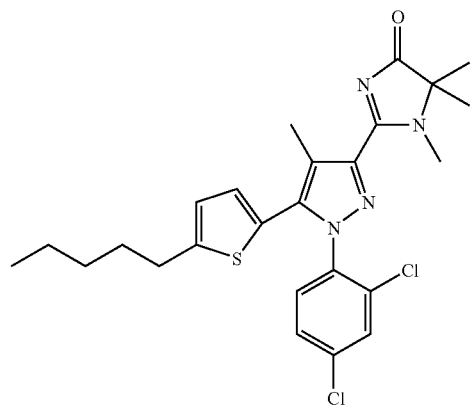
45
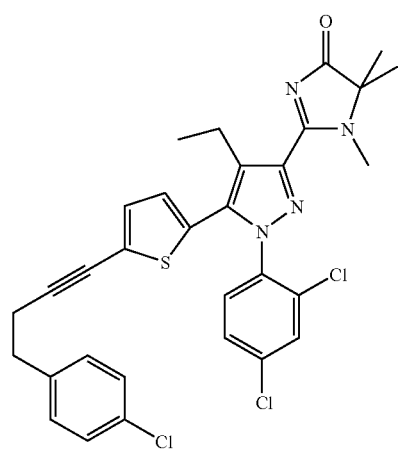
46
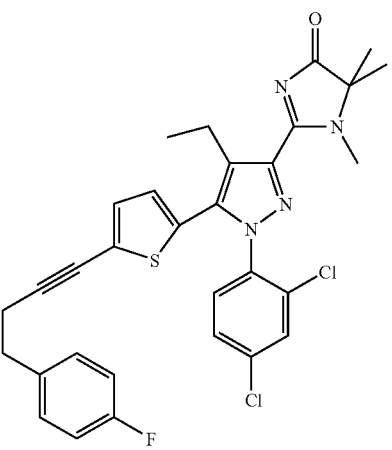
47
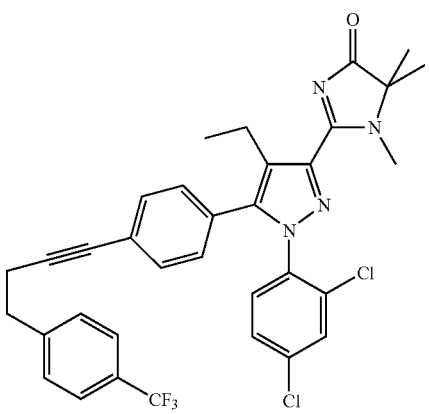
48
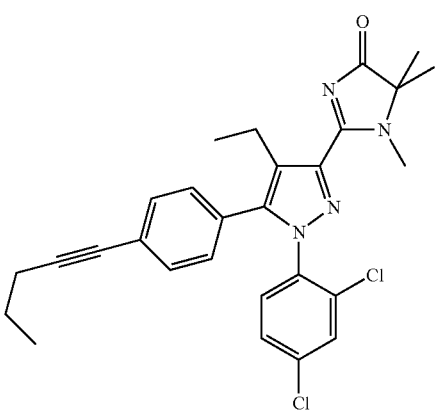

15
-continued

49

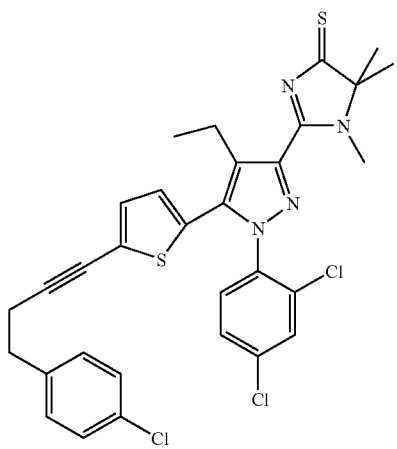

50

51

16
-continued

52

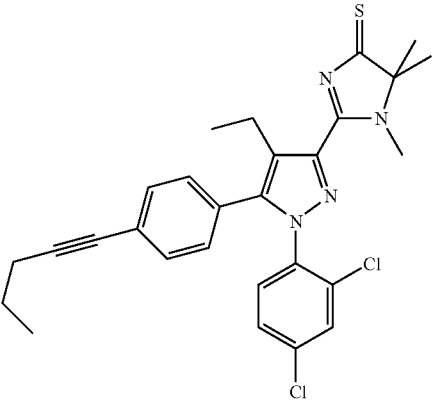

The imidazol-4-one or imidazole-4-thione compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-4 below show transformations for synthesizing compounds of this invention.

Compounds 6-22 were prepared according to a general synthetic method shown in Scheme 1 below using compound 6 and its corresponding thioketone 21 as typical examples. Treatment of 1-(4-chlorophenyl)-propan-1-one (1a) with diethyl oxalate in the presence of LHMDS as a base gave rise to lithium salt 2a in 80% yield, which in turn was coupled with 2,4-dichlorophenylhydrazine hydrochloride in ethanol followed by intramolecular cyclization in acetic acid under refluxing conditions to provide ester 3a in 49% yield over two steps. Compound 3a thus obtained was subjected to basic hydrolysis under standard conditions to give carboxylic acid 4a in 94% yield, which was then treated with oxalyl chloride to activate the carboxylic group. The resulting acid chloride was coupled with 2-methyl-2-methylamino-propionamide (5a) to afford the crude amide intermediate. Without purification, this intermediate underwent intramolecular cyclization in the presence of sodium methoxide to furnish the desired product 6 in 55% yield over two steps. Further treatment of compound 6 with Lawesson's reagent afforded the corresponding thioketone 21 in 77% yield.

Scheme 1

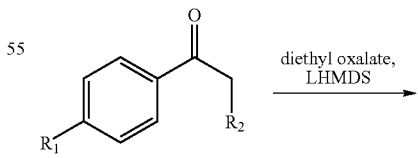

1a: $R_1$ = Cl, $R_2$ = Me
1b: $R_1$ = Cl, $R_2$ = H
1c: $R_1$ = Cl, $R_2$ = Et
1d: $R_1$ = Br, $R_2$ = Me
1e: $R_1$ = Br, $R_2$ = Et
1f: $R_1$ = OMe, $R_2$ = Me
1g: $R_1$ = F, $R_2$ = Me
1h: $R_1$ = CF$_3$, $R_2$ = Me

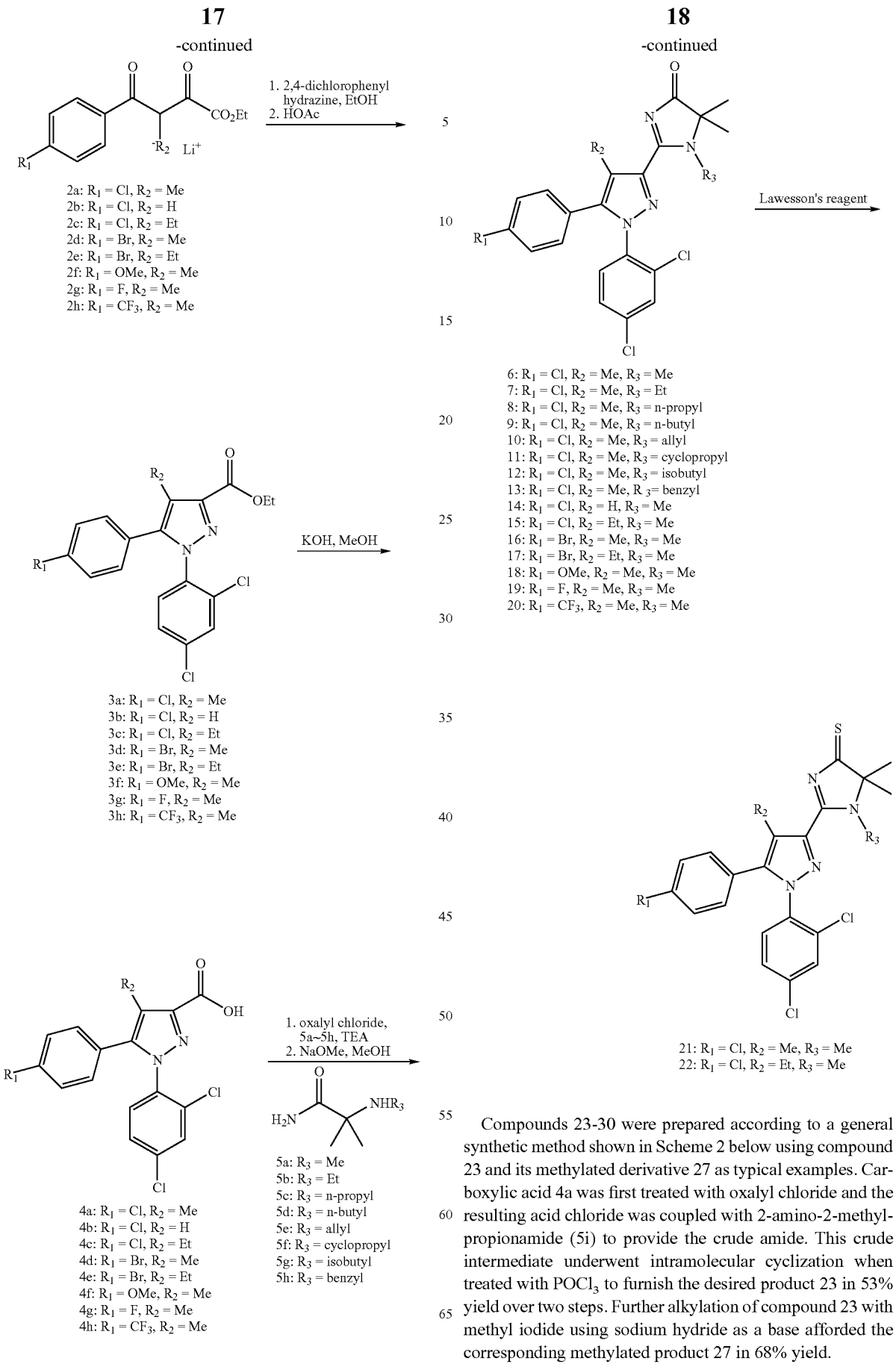

Compounds 23-30 were prepared according to a general synthetic method shown in Scheme 2 below using compound 23 and its methylated derivative 27 as typical examples. Carboxylic acid 4a was first treated with oxalyl chloride and the resulting acid chloride was coupled with 2-amino-2-methyl-propionamide (5i) to provide the crude amide. This crude intermediate underwent intramolecular cyclization when treated with $POCl_3$ to furnish the desired product 23 in 53% yield over two steps. Further alkylation of compound 23 with methyl iodide using sodium hydride as a base afforded the corresponding methylated product 27 in 68% yield.

Scheme 2

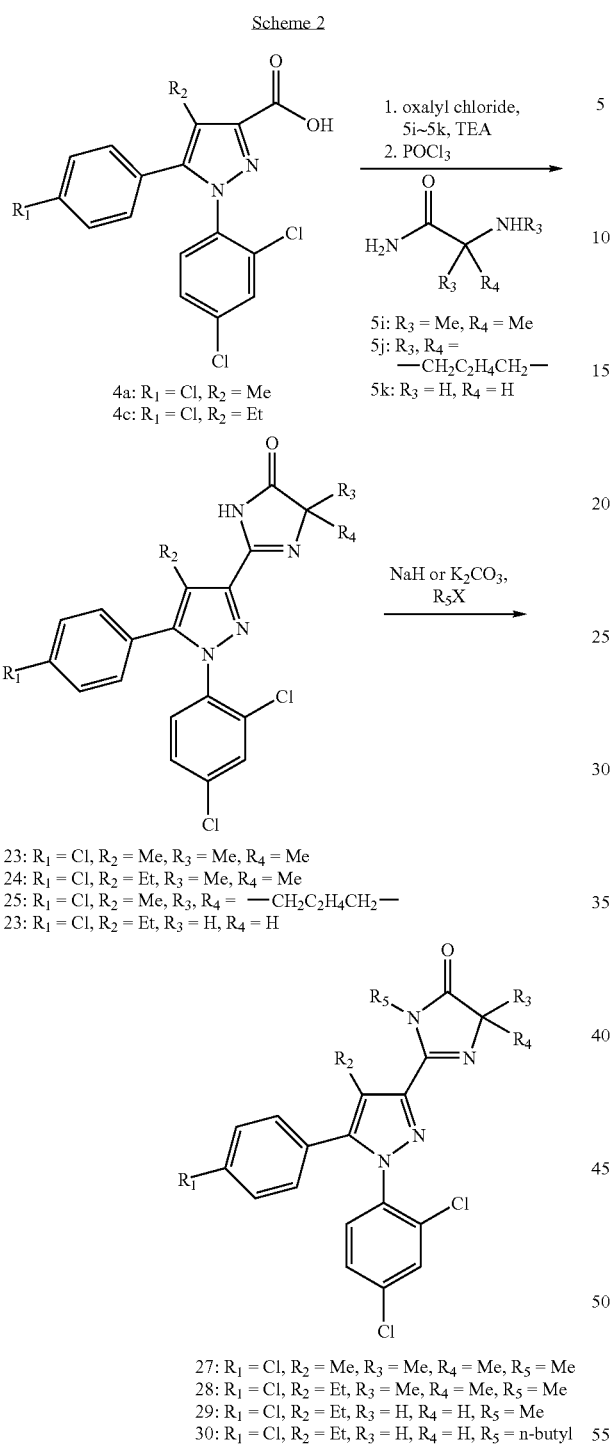

4a: $R_1$ = Cl, $R_2$ = Me
4c: $R_1$ = Cl, $R_2$ = Et 1. oxalyl chloride, 5i~5k, TEA
2. POCl$_3$ 5i: $R_3$ = Me, $R_4$ = Me
5j: $R_3$, $R_4$ = —CH$_2$C$_2$H$_4$CH$_2$—
5k: $R_3$ = H, $R_4$ = H 23: $R_1$ = Cl, $R_2$ = Me, $R_3$ = Me, $R_4$ = Me
24: $R_1$ = Cl, $R_2$ = Et, $R_3$ = Me, $R_4$ = Me
25: $R_1$ = Cl, $R_2$ = Me, $R_3$, $R_4$ = —CH$_2$C$_2$H$_4$CH$_2$—
23: $R_1$ = Cl, $R_2$ = Et, $R_3$ = H, $R_4$ = H NaH or K$_2$CO$_3$, R$_5$X 27: $R_1$ = Cl, $R_2$ = Me, $R_3$ = Me, $R_4$ = Me, $R_5$ = Me
28: $R_1$ = Cl, $R_2$ = Et, $R_3$ = Me, $R_4$ = Me, $R_5$ = Me
29: $R_1$ = Cl, $R_2$ = Et, $R_3$ = H, $R_4$ = H, $R_5$ = Me
30: $R_1$ = Cl, $R_2$ = Et, $R_3$ = H, $R_4$ = H, $R_5$ = n-butyl Compounds 33-42 were prepared according to a general synthetic method shown in Scheme 3 below using compound 34 and its corresponding thioketone 40 as typical examples. Starting materials 31a-31g are readily prepared based on the procedures reported by Shia et al. (*Journal of Medicinal Chemistry*, 2008, 51, 5397-5412). Compound 31b was reacted with oxalyl chloride to activate the carboxylic group and the resulting acid chloride was coupled with 2-methyl-2-methylamino-propionamide (5a) to afford the crude amide intermediate. Without purification, this crude intermediate underwent intramolecular cyclization by treatment with sodium methoxide to give product 34 in 51% yield over two steps. Further treatment of 34 with Lawesson's reagent afforded the corresponding thioketone 40 in 73% yield.

Scheme 3

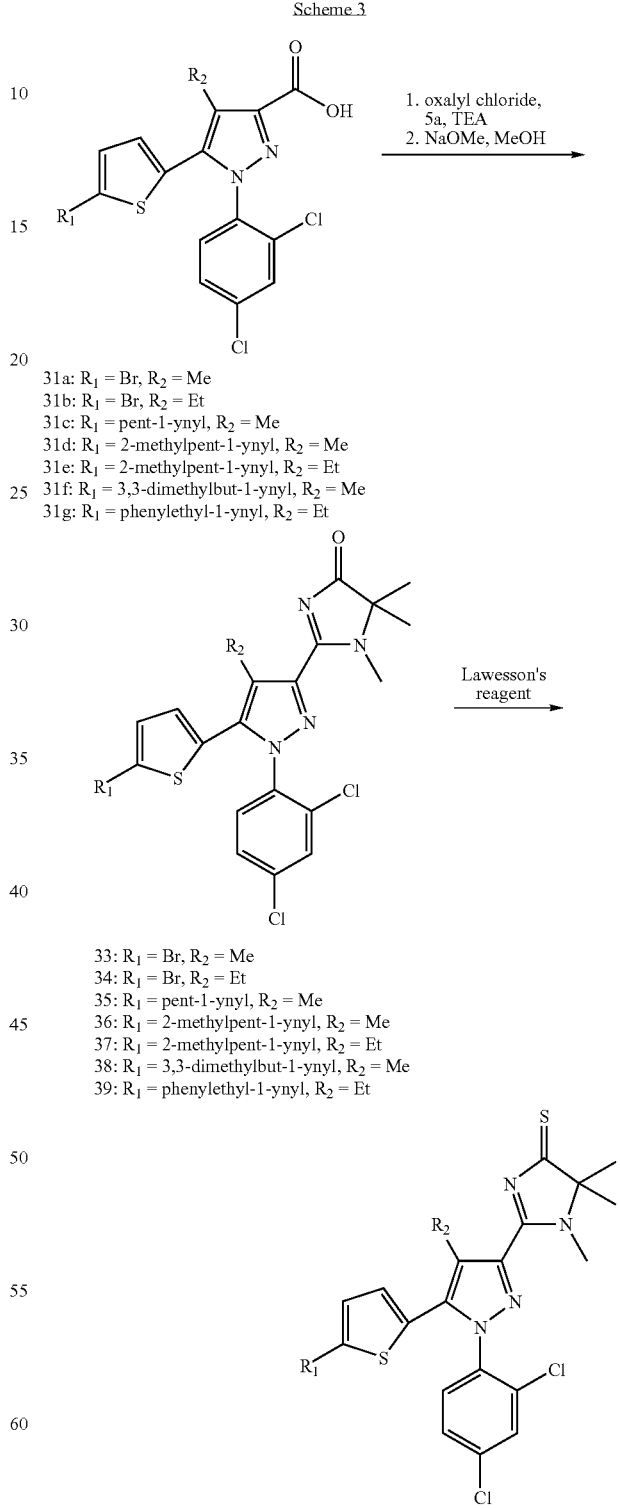

31a: $R_1$ = Br, $R_2$ = Me
31b: $R_1$ = Br, $R_2$ = Et
31c: $R_1$ = pent-1-ynyl, $R_2$ = Me
31d: $R_1$ = 2-methylpent-1-ynyl, $R_2$ = Me
31e: $R_1$ = 2-methylpent-1-ynyl, $R_2$ = Et
31f: $R_1$ = 3,3-dimethylbut-1-ynyl, $R_2$ = Me
31g: $R_1$ = phenylethyl-1-ynyl, $R_2$ = Et 1. oxalyl chloride, 5a, TEA
2. NaOMe, MeOH 33: $R_1$ = Br, $R_2$ = Me
34: $R_1$ = Br, $R_2$ = Et
35: $R_1$ = pent-1-ynyl, $R_2$ = Me
36: $R_1$ = 2-methylpent-1-ynyl, $R_2$ = Me
37: $R_1$ = 2-methylpent-1-ynyl, $R_2$ = Et
38: $R_1$ = 3,3-dimethylbut-1-ynyl, $R_2$ = Me
39: $R_1$ = phenylethyl-1-ynyl, $R_2$ = Et Lawesson's reagent 40: $R_1$ = Br, $R_2$ = Et
41: $R_1$ = 2-methylpent-1-ynyl, $R_2$ = Me
42: $R_1$ = 2-methylpent-1-ynyl, $R_2$ = Et Compounds 43 and 44 were prepared according to a general synthetic method shown in Scheme 4 below. Starting material 32 was prepared through the synthetic method reported by Shia et al. (*Journal of Medicinal Chemistry*, 2008, 51, 5397-5412). Compound 32 was reacted with oxalyl chloride to activate the carboxylic group and the resulting acid chloride was coupled with 2-methyl-2-methylamino-propionamide (5a) to give the crude amide, which in turn, without purification, underwent cyclization when treated with sodium methoxide to furnish compound 43 in 70% yield over two steps. Further transformation of compound 43 using catalyst Pd—C under one atmosphere of hydrogen afforded the corresponding saturated product 44 in 62% yield.

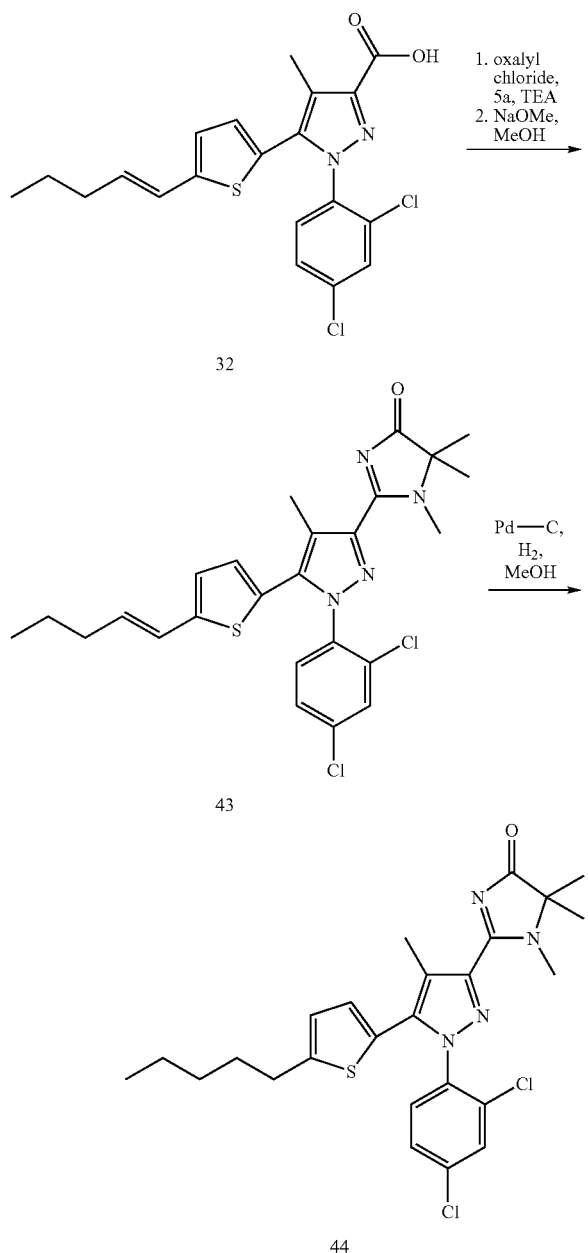

Scheme 4

The imidazol-4-one or imidazole-4-thione compounds of this invention can also be synthesized in manners similar to those outlined in Schemes 1-4 with necessary modifications as recognized by those skilled in the art.

An imidazol-4-one or imidazole-4-thione compound thus synthesized can be further purified by flash column chromatography, high performance liquid chromatography, crystallization, or any other suitable methods.

The imidazol-4-one or imidazole-4-thione compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the imidazol-4-one or imidazole-4-thione compounds of this invention and a pharmaceutically acceptable carrier, and (2) a method for treating a cannabinoid receptor-mediated disorder by administering to a subject in need of this treatment an effective amount of such an imidazol-4-one or imidazole-4-thione compound.

As used herein, the term "treating" refers to administering an imidazol-4-one or imidazole-4-thione compound to a subject that has a cannabinoid receptor-mediated disorder, or has a symptom of or a predisposition toward such a disorder, with the purpose to cure, heal, alleviate, relieve, alter, remedy, ameliorate, improve, or affect the above-described disorder, the symptoms of or the predisposition toward it. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An imidazol-4-one or imidazole-4-thione compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents, which form more soluble complexes with the imidazol-4-one or imidazole-4-thione compounds, or more solubilizing agents, can be utilized as pharmaceutical carriers for delivery of the active compounds. Examples of other carriers include colloidal silicon dioxide, magnesium stearate, sodium lauryl sulfate, and D&C Yellow #10.

The imidazol-4-one or imidazole-4-thione compounds described above can be preliminarily screened for their efficacy in treating above-described diseases by an in vitro assay and then confirmed by animal experiments and clinic trials. Other methods will also be apparent to those of ordinary skill in the art.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of lithium salt of 4-(4-chloro-phenyl)-3-methyl-2,4-dioxo-butyric acid ethyl ester (2a)

To a magnetically stirred solution of lithium bis-(trimethylsilyl)amide (16.0 mL, 1.0 M in THF, 16 mmol) in diethyl ether (45 mL) at −78° C. was added a solution of 1-(4-chloro-phenyl)-propan-1-one (1a) (2.0 g, 11.86 mmol) in diethyl ether (15 mL) dropwise under an argon atmosphere. After the mixture was stirred at the same temperature for an additional period of 45 min, diethyl oxalate (2.0 g, 13.69 mmol) was added dropwise. The reaction mixture was allowed to warm to room temperature and stirred for another 16 h. The precipitate formed was collected by filtration, washed with diethyl ether, and dried under vacuum to afford the crude lithium salt 2a (2.6 g, 80%) as a yellowish solid.

Example 2

Synthesis of lithium salt of 4-(4-chloro-phenyl)-2,4-dioxo-butyric acid ethyl ester (2b)

Compound 2b was synthesized from 1-(4-chloro-phenyl)-ethanone (1b) (2.0 g, 12.93 mmol) as a yellowish solid (2.3 g, 68%) in a manner similar to that described in Example 1.

Example 3

Synthesis of lithium salt of 3-(4-chloro-benzoyl)-2-oxo-pentanoic acid ethyl ester (2c)

Compound 2c was synthesized from 1-(4-chloro-phenyl)-butan-1-one (1c) (2.0 g, 10.95 mmol) as a yellowish solid (2.1 g, 66%) in a manner similar to that described in Example 1.

Example 4

Synthesis of lithium salt of 4-(4-bromo-phenyl)-3-methyl-2,4-dioxo-butyric acid ethyl ester (2d)

Compound 2d was synthesized from 1-(4-bromo-phenyl)-propan-1-one (1d) (2.0 g, 9.39 mmol) as a yellowish solid (2.2 g, 73%) in a manner similar to that described in Example 1.

Example 5

Synthesis of lithium salt of 3-(4-bromo-benzoyl)-2-oxo-pentanoic acid ethyl ester (2e)

Compound 2e was synthesized from 1-(4-bromo-phenyl)-butan-1-one (1e) (2.0 g, 8.81 mmol) as a yellowish solid (1.9 g, 65%) in a manner similar to that described in Example 1.

Example 6

Synthesis of lithium salt of 4-(4-methoxy-phenyl)-3-methyl-2,4-dioxo-butyric acid ethyl ester (2f)

Compound 2f was synthesized from 1-(4-methoxy-phenyl)-propan-1-one (1f) (2.0 g, 12.19 mmol) as a yellowish solid (2.6 g, 79%) in a manner similar to that described in Example 1.

Example 7

Synthesis of lithium salt of 4-(4-fluoro-phenyl)-3-methyl-2,4-dioxo-butyric acid ethyl ester (2g)

Compound 2g was synthesized from 1-(4-fluoro-phenyl)-propan-1-one (1g) (2.0 g, 13.16 mmol) as a yellowish solid (2.4 g, 71%) in a manner similar to that described in Example 1.

Example 8

Synthesis of lithium salt of 3-methyl-2,4-dioxo-4-(4-trifluoromethyl-phenyl)-butyric acid ethyl ester (2h)

Compound 2h was synthesized from 1-(4-trifluoromethyl-phenyl)-propan-1-one (1h) (2.0 g, 9.90 mmol) as a yellowish solid (2.2 g, 72%) in a manner similar to that described in Example 1.

Example 9

Synthesis of 5-(4-chloro-phenyl)-1-(2,4-dichloro-phenyl)-4-methyl-1H-pyrazole-3-carboxylic acid ethyl ester (3a)

To a solution of the lithium salt 2a (2.60 g, 9.47 mmol) in ethanol (35 mL) was added 2,4-dichlorophenylhydrazine hydrochloride (2.2 g, 10.30 mmol) in one portion at room temperature. The resulting mixture was stirred at the same temperature for 20 h. After the reaction was complete, the precipitate was collected by filtration, washed with ethanol and diethyl ether, and dried under vacuum to give a light-yellow solid. This crude solid, without purification, was dissolved in acetic acid (30 mL) and heated to reflux for 24 h. The reaction mixture was poured into ice water and the resulting mixture was extracted with ethyl acetate (2×30 mL). The combined extracts were washed with water, saturated aqueous sodium bicarbonate, and brine, dried over anhydrous sodium sulfate, filtered, and concentrated. Purification of the crude residue by flash chromatography on silica gel with hexanes/ethyl acetate (9:1) gave the ester 3a (1.9 g, 49% over two steps) as a white solid.

Example 10

Synthesis of 5-(4-chloro-phenyl)-1-(2,4-dichloro-phenyl)-1H-pyrazole-3-carboxylic acid ethyl ester (3b)

Compound 3b was synthesized from 2b (2.3 g, 8.83 mmol) as a white solid (1.7 g, 49%) in a manner similar to that described in Example 9.

Example 11

Synthesis of 5-(4-chloro-phenyl)-1-(2,4-dichloro-phenyl)-4-ethyl-1H-pyrazole-3-carboxylic acid ethyl ester (3c)

Compound 3c was synthesized from 2c (2.1 g, 7.28 mmol) as a white solid (1.1 g, 36%) in a manner similar to that described in Example 9.

Example 12

Synthesis of 5-(4-bromo-phenyl)-1-(2,4-dichloro-phenyl)-4-methyl-1H-pyrazole-3-carboxylic acid ethyl ester (3d)

Compound 3d was synthesized from 2d (2.2 g, 6.89 mmol) as a white solid (1.5 g, 48%) in a manner similar to that described in Example 9.

Example 13

Synthesis of 5-(4-bromo-phenyl)-1-(2,4-dichloro-phenyl)-4-ethyl-1H-pyrazole-3-carboxylic acid ethyl ester (3e)

Compound 3e was synthesized from 2e (1.9 g, 5.70 mmol) as a white solid (1.0 g, 37%) in a manner similar to that described in Example 9.

Example 14

Synthesis of 1-(2,4-dichloro-phenyl)-5-(4-methoxy-phenyl)-4-methyl-1H-pyrazole-3-carboxylic acid ethyl ester (3f)

Compound 3f was synthesized from 2f (2.6 g, 9.62 mmol) as a white solid (1.6 g, 41%) in a manner similar to that described in Example 9.

Example 15

Synthesis of 1-(2,4-dichloro-phenyl)-5-(4-fluoro-phenyl)-4-methyl-1H-pyrazole-3-carboxylic acid ethyl ester (3g)

Compound 3g was synthesized from 2g (2.4 g, 9.30 mmol) as a white solid (1.5 g, 41%) in a manner similar to that described in Example 9.

Example 16

Synthesis of 1-(2,4-dichloro-phenyl)-5-(4-trifluoromethyl-phenyl)-4-methyl-1H-pyrazole-3-carboxylic acid ethyl ester (3h)

Compound 3h was synthesized from 2h (2.2 g, 7.14 mmol) as a white solid (1.5 g, 47%) in a manner similar to that described in Example 9.

Example 17

Synthesis of 5-(4-chloro-phenyl)-1-(2,4-dichloro-phenyl)-4-methyl-1H-pyrazole-3-carboxylic acid (4a)

To a solution of the ester 3a (1.0 g, 2.44 mmol) in methanol (25 mL) was added potassium hydroxide (1.0 g, 17.86 mmol) in one portion. The resulting mixture was heated at 60° C. for 4 h. The reaction mixture was then poured into ice water, and the pH of the mixture was adjusted to acidic with addition of 10% hydrochloric acid. The precipitate formed was collected by filtration, washed with water, and dried under vacuum to give carboxylic acid 4a (0.88 g, 94%) as a white solid.

Example 18

Synthesis of 5-(4-chloro-phenyl)-1-(2,4-dichloro-phenyl)-1H-pyrazole-3-carboxylic acid (4b)

Compound 4b was synthesized from 3b (0.97 g, 2.45 mmol) as a white solid (0.84 g, 93%) in a manner similar to that described in Example 17.

Example 19

Synthesis of 5-(4-chloro-phenyl)-1-(2,4-dichloro-phenyl)-4-ethyl-1H-pyrazole-3-carboxylic acid (4c)

Compound 4c was synthesized from 3c (1.02 g, 2.41 mmol) as a white solid (0.85 g, 89%) in a manner similar to that described in Example 17.

Example 20

Synthesis of 5-(4-bromo-phenyl)-1-(2,4-dichloro-phenyl)-4-methyl-1H-pyrazole-3-carboxylic acid (4d)

Compound 4d was synthesized from 3d (1.02 g, 2.25 mmol) as a white solid (0.81 g, 85%) in a manner similar to that described in Example 17.

Example 21

Synthesis of 5-(4-bromo-phenyl)-1-(2,4-dichloro-phenyl)-4-ethyl-1H-pyrazole-3-carboxylic acid (4e)

Compound 4e was synthesized from 3e (0.94 g, 2.01 mmol) as a white solid (0.78 g, 88%) in a manner similar to that described in Example 17.

Example 22

Synthesis of 1-(2,4-dichloro-phenyl)-5-(4-methoxy-phenyl)-4-methyl-1H-pyrazole-3-carboxylic acid (4f)

Compound 4f was synthesized from 3f (1.01 g, 2.49 mmol) as a white solid (0.79 g, 84%) in a manner similar to that described in Example 17.

Example 23

Synthesis of 1-(2,4-dichloro-phenyl)-5-(4-fluoro-phenyl)-4-methyl-1H-pyrazole-3-carboxylic acid (4g)

Compound 4g was synthesized from 3g (0.98 g, 2.49 mmol) as a white solid (0.84 g, 92%) in a manner similar to that described in Example 17.

Example 24

Synthesis of 1-(2,4-dichloro-phenyl)-4-methyl-5-(4-trifluoromethyl-phenyl)-1H-pyrazole-3-carboxylic acid (4h)

Compound 4h was synthesized from 3h (1.07 g, 2.41 mmol) as a white solid (0.88 g, 88%) in a manner similar to that described in Example 17.

Example 25

Synthesis of 2-bromo-2-methylpropanamide

To a vigorously stirred solution of 28% $NH_4OH$ (25 mL, 411.76 mmol) were added sequentially $H_2O$ (25 mL) and 2-bromo-2-methyl propanoyl bromide (10.0 g, 43.50 mmol) dropwise at 0° C. The reaction mixture was allowed to warm to room temperature and stirred for an additional period of 2 h. The precipitate formed was collected by filtration, washed with water, and dried under vacuum to afford 2-bromo-2-methylpropanamide (6.1 g, 84%) as a white solid.

Example 26

Synthesis of 2-methyl-2-methylamino-propionamide (5a)

To a mixture of 2-bromo-2-methyl-propionamide (9.12 g, 54.93 mmol) and silver (I) oxide (14.4 g, 102.9 mmol) in THF (120 mL) was added methyl amine (60 mL, 2M in THF, 120 mmol) dropwise at room temperature. The resulting mixture was stirred at the same temperature for 15 h. The reaction mixture was filtered, and the filtrate was concentrated. The residue was purified by flash chromatography on silica gel with ethyl acetate/methanol (4:1) to give 5a (3.02 g, 47%). $^1$H NMR (400 MHz, $CDCl_3$) δ 2.31 (s, 3H), 1.32 (s, 3H), 1.29 (s, 3H).

Example 27

Synthesis of 2-ethylamino-2-methyl-propionamide (5b)

Compound 5b was synthesized from 2-bromo-2-methyl-propionamide (2.03 g, 12.23 mmol) as an off-white solid (0.81 g, 51%) in a manner similar to that described in Example 26.

Example 28

Synthesis of 2-methyl-2-propylamino-propionamide (5c)

Compound 5c was synthesized from 2-bromo-2-methyl-propionamide (1.04 g, 6.26 mmol) as an off-white solid (0.41 g, 45%) in a manner similar to that described in Example 26. $^1$H NMR (600 MHz, $CDCl_3$) δ 7.21 (br s, 1H), 5.71 (br s, 1H), 2.46-2.44 (m, 2H), 1.44-1.42 (m, 2H), 1.29 (s, 6H), 0.91-0.89 (m, 3H); ESMS m/z: 145.3 (M+1).

Example 29

Synthesis of 2-butylamino-2-methyl-propionamide (5d)

Compound 5d was synthesized from 2-bromo-2-methyl-propionamide (0.98 g, 5.90 mmol) as an off-white solid (0.37 g, 40%) in a manner similar to that described in Example 26. $^1$H NMR (600 MHz, $CDCl_3$) δ 7.15 (br s, 1H), 6.27 (br s, 1H), 2.43 (t, 2H), 1.37-1.26 (m, 10H), 0.83 (d, 3H); ESMS m/z: 159.4 (M+1).

Example 30

Synthesis of 2-allylamino-2-methyl-propionamide (5e)

Compound 5e was synthesized from 2-bromo-2-methyl-propionamide (1.10 g, 6.63 mmol) as an off-white solid (0.39 g, 41%) in a manner similar to that described in Example 26. $^1$H NMR (600 MHz, $CDCl_3$) δ 7.13 (br s, 1H), 6.12 (br s, 1H), 5.86-5.82 (m, 1H), 5.17-5.14 (m, 1H), 5.03-5.01 (m, 1H), 3.12-3.10 (m, 2H), 1.28 (d, 6H); ESMS m/z: 143.0 (M+1).

Example 31

Synthesis of 2-cyclopropylamino-2-methyl-propionamide (5f)

Compound 5f was synthesized from 2-bromo-2-methyl-propionamide (0.96 g, 5.78 mmol) as an off-white solid (0.36 g, 44%) in a manner similar to that described in Example 26. $^1$H NMR (400 MHz, $CDCl_3$) δ 6.88 (br s, 1H), 5.85 (br s, 1H), 2.05-2.10 (m, 1H), 1.34 (s, 6H), 0.45-0.41 (m, 2H), 0.34-0.30 (m, 2H); ESMS m/z: 143.3 (M+1).

Example 32

Synthesis of 2-isobutylamino-2-methyl-propionamide (5g)

Compound 5g was synthesized from 2-bromo-2-methyl-propionamide (1.05 g, 6.32 mmol) as an off-white solid (0.46 g, 46%) in a manner similar to that described in Example 26. $^1$H NMR (400 MHz, $CDCl_3$) δ 7.15 (br s, 1H), 6.27 (br s, 1H), 2.14-2.11 (m, 2H), 1.56-1.59 (m, 1H), 1.24 (s, 6H), 0.85 (d, 6H); ESMS m/z: 159.2 (M+1).

Example 33

Synthesis of 2-benzylamino-2-methyl-propionamide (5h)

Compound 5h was synthesized from 2-bromo-2-methyl-propionamide (1.04 g, 6.26 mmol) as a white solid (0.50 g, 42%) in a manner similar to that described in Example 26. $^1$H NMR (400 MHz, CDCl$_3$) δ 7.23 (m, 5H), 3.65 (s, 1H), 3.64 (s, 1H), 1.37 (s, 3H), 1.36 (s, 3H).

Example 34

Synthesis of 2-amino-2-methyl-propionamide hydrochloride salt (5i)

To a solution of 2-tert-butoxycarbonylamino-2-methyl-propionic acid (0.99 g, 4.87 mmol) in dichloromethane (25 mL) were sequentially added EDCI (1.4 g, 7.30 mmol) and HOBt (1.0 g, 7.40 mmol) in one portion. The resulting mixture was stirred at room temperature for 2 h, then bubbled with NH$_3$ (g) for 10 min. After amidation was complete, the reaction mixture was poured into ice water, and the resulting mixture was extracted with ethyl acetate (2×50 mL). The combined extracts were washed with brine, dried over anhydrous sodium sulfate, filtered, and concentrated to give the crude product, which in turn, without purification, was subjected to hydrolysis with HCl (17 mL, 2 M in diethylether) in dichloromethane (7 mL) at room temperature for 15 h. The mixture was filtered and the solid residue was dried under vacuum to give 5i (0.41 g, 61%) as a white solid. $^1$H NMR (400 MHz, CDCl$_3$) δ 1.59 (s, 6H).

Example 35

Synthesis of 1-amino-cyclopentanecarboxylic acid amide hydrochloride salt (5j)

To a solution of 1-amino-cyclopentanecarboxylic acid (1.03 g, 7.97 mmol) in H$_2$O (16 mL) were added Di-tent-butyl dicarbonate (2.5 g, 11.46 mmol) and sodium hydroxide (0.65 g, 16.25 mmol) in one portion. The resulting mixture was stirred at room temperature for 15 h. The reaction mixture was acidified with 10% hydrochloric acid and then extracted with ethyl acetate (2×50 mL). The combined extracts were washed with brine, dried over anhydrous sodium sulfate, filtered, and concentrated to give the crude 1-tert-Butoxycarbonylamino-cyclopentanecarboxylic acid. Without purification, the crude carboxylic product thus obtained was treated with EDCI (1.5 g, 7.82 mmol) and HOBt (1.1 g, 8.14 mmol) in dichloromethane (25 mL) at room temperature for 2 h, and then NH$_3$(g) was introduced into the solution for 30 min. After amidation was complete, the reaction mixture was poured into ice water, and extracted with ethyl acetate (2×50 mL). The combined extracts were washed with brine, dried over anhydrous sodium sulfate, filtered, and concentrated to give the crude amide product, which was subjected to hydrolysis with HCl (14 mL, 2 M in diethylether, 28 mmol) in dichloromethane (7 mL) at room temperature for 15 h. The reaction mixture was filtered and the solid residue was dried under vacuum to afford 5j (0.45 g, 34% over three steps).

Example 36

Synthesis of 2-[5-(4-chloro-phenyl)-1-(2,4-dichloro-phenyl)-4-methyl-1H-pyrazol-3-yl]-1,5,5-trimethyl-1,5-dihydro-imidazol-4-one (6)

To a solution of 4a (1.0 g, 2.62 mmol) in toluene (30 mL) at 0° C. were sequentially added DMF (0.2 mL) and oxalyl chloride (1.48 g, 11.66 mmol) dropwise. The resulting mixture was allowed to warm to room temperature and stirred for 1 h, then transferred slowly to a mixture of 5a (0.50 g, 4.30 mmol) and triethylamine (0.42 g, 4.16 mmol) in THF (30 mL) at 0° C. After the mixture was warmed and stirred at room temperature for 15 h, the reaction was quenched with water and extracted with ethyl acetate (2×30 mL). The combined extracts were washed with brine, dried over anhydrous sodium sulfate, filtered, and concentrated to give the crude residue (1.22 g), which without purification, underwent intramolecular cyclization by treatment with sodium methoxide (270 mg, 5.00 mmol) in methanol (30 mL) at 60° C. for 4 h. After the reaction was complete, the reaction mixture was concentrated and poured into ice water and the resulting mixture was extracted with ethyl acetate (2×30 mL). The combined extracts were washed with brine, dried over anhydrous sodium sulfate, filtered, and concentrated. The residue was purified by flash chromatography on silica gel with hexanes/ethyl acetate (1:1) to afford the desired product 6 (0.67 g, 55%) as a white solid. $^1$H NMR (400 MHz, CDCl$_3$) δ 7.41 (d, 1H), 7.25 (d, 2H), 7.22 (dd, 1H), 7.12 (d, 1H), 7.01 (d, 2H), 3.42 (s, 3H), 2.35 (s, 3H), 1.37 (s, 6H); ESMS m/z: 461.0 (M+1).

Example 37

Synthesis of 2-[5-(4-chloro-phenyl)-1-(2,4-dichloro-phenyl)-4-methyl-1H-pyrazol-3-yl]-1-ethyl-5,5-dimethyl-1,5-dihydro-imidazol-4-one (7)

Compound 7 was synthesized from 4a (251 mg, 0.66 mmol) and 5b (140 mg, 1.08 mmol) as a white solid (110 mg, 35%) in a manner similar to that described in Example 36. $^1$H NMR (400 MHz, CDCl$_3$) δ 7.43 (d, 1H), 7.28 (d, 2H), 7.25 (dd, H), 7.14 (d, 1H), 7.04 (d, 2H), 3.90 (q, 2H), 2.37 (s, 3H), 1.41 (s, 6H), 1.27 (t, 3H); ESMS m/z: 475.0 (M+1).

Example 38

Synthesis of 2-[5-(4-chloro-phenyl)-1-(2,4-dichloro-phenyl)-4-methyl-1H-pyrazol-3-yl]-5,5-dimethyl-1-propyl-1,5-dihydro-imidazol-4-one (8)

Compound 8 was synthesized from 4a (250 mg, 0.66 mmol) and 5c (150 mg, 1.04 mmol) as a white solid (97 mg, 30%) in a manner similar to that described in Example 36. $^1$H NMR (600 MHz, CDCl$_3$) δ 7.45 (d, 1H), 7.28-7.23 (m, 3H), 7.11 (d, 1H), 7.05 (d, 2H), 3.76-3.73 (m, 2H), 2.37 (s, 3H), 1.72-1.68 (m, 2H), 1.41 (s, 6H), 0.81 (t, 3H); ESMS m/z: 489.1 (M+1).

Example 39

Synthesis of 1-butyl-2-[5-(4-chloro-phenyl)-1-(2,4-dichloro-phenyl)-4-methyl-1H-pyrazol-3-yl]-5,5-dimethyl-1,5-dihydro-imidazol-4-one (9)

Compound 9 was synthesized from 4a (252 mg, 0.66 mmol) and 5d (161 mg, 1.01 mmol) as a white solid (141 mg, 42%) in a manner similar to that described in Example 36. $^1$H NMR (600 MHz, CDCl$_3$) δ 7.44 (d, 1H), 7.29-7.24 (m, 3H), 7.13 (d, 1H), 7.05 (d, 2H), 3.80-3.78 (m, 2H), 2.39 (s, 3H), 1.69-1.64 (m, 2H), 1.40 (s, 6H), 1.26-1.22 (m, 2H), 0.81 (t, 3H); ESMS m/z: 503.1 (M+1).

Example 40

Synthesis of 1-allyl-2-[5-(4-chloro-phenyl)-1-(2,4-dichloro-phenyl)-4-methyl-1H-pyrazol-3-yl]-5,5-dimethyl-1,5-dihydro-imidazol-4-one (10)

Compound 10 was synthesized from 4a (253 mg, 0.66 mmol) and 5e (148 mg, 1.05 mmol) as a white solid (171 mg, 53%) in a manner similar to that described in Example 36. $^1$H NMR (600 MHz, CDCl$_3$) δ 7.41 (d, 1H), 7.27-7.23 (m, 3H), 7.13 (d, 1H), 7.04 (d, 2H), 5.93-5.88 (m, 1H), 5.13-5.07 (m, 2H), 4.54 (d, 2H), 2.37 (s, 3H), 1.40 (s, 6H); ESMS m/z: 487.1 (M+1).

Example 41

Synthesis of 2-[5-(4-chloro-phenyl)-1-(2,4-dichloro-phenyl)-4-methyl-1H-pyrazol-3-yl]-1-cyclopropyl-5,5-dimethyl-1,5-dihydro-imidazol-4-one (11)

Compound 11 was synthesized from 4a (248 mg, 0.66 mmol) and 5f (148 mg, 1.05 mmol) as a white solid (122 mg, 38%) in a manner similar to that described in Example 36. $^1$H NMR (600 MHz, CDCl$_3$) δ 7.42 (d, 1H), 7.28-7.26 (m, 3H), 7.21 (d, 1H), 7.07 (d, 2H), 2.91-2.89 (m, 1H), 2.29 (s, 3H), 1.49 (s, 6H), 0.88-0.86 (m, 2H), 0.76-0.73 (m, 2H); ESMS m/z: 487.0 (M+1).

Example 42

Synthesis of 2-[5-(4-chloro-phenyl)-1-(2,4-dichloro-phenyl)-4-methyl-1H-pyrazol-3-yl]-1-isobutyl-5,5-dimethyl-1,5-dihydro-imidazol-4-one (12)

Compound 12 was synthesized from 4a (248 mg, 0.66 mmol) and 5g (160 mg, 1.01 mmol) as a white solid (110 mg, 33%) in a manner similar to that described in Example 36. $^1$H NMR (600 MHz, CDCl$_3$) δ 7.46 (d, 1H), 7.29-7.24 (m, 3H), 7.11 (d, 1H), 7.06 (d, 2H), 3.78-3.75 (m, 2H), 2.34 (s, 3H), 2.03-2.01 (m, 1H), 1.44 (s, 6H), 0.85-0.82 (d, 6H); ESMS m/z: 503.1 (M+1).

Example 43

Synthesis of 1-benzyl-2-[5-(4-chloro-phenyl)-1-(2,4-dichloro-phenyl)-4-methyl-1H-pyrazol-3-yl]-5,5-dimethyl-1,5-dihydro-imidazol-4-one (13)

Compound 13 was synthesized from 4a (250 mg, 0.66 mmol) and 5h (189 mg, 0.99 mmol) as a white solid (152 mg, 43%) in a manner similar to that described in Example 36. $^1$H NMR (400 MHz, CDCl$_3$) δ 7.38 (d, 1H), 7.31 (d, 2H), 7.26 (m, 5H), 7.20 (dd, 1H), 7.04 (d, 2H), 7.01 (d, 1H), 5.29 (s, 2H), 2.45 (s, 3H), 1.31 (s, 6H); ESMS m/z: 537.1 (M+1).

Example 44

Synthesis of 2-[5-(4-chloro-phenyl)-1-(2,4-dichloro-phenyl)-1H-pyrazol-3-yl]-1,5,5-trimethyl-1,5-dihydro-imidazol-4-one (14)

Compound 14 was synthesized from 4b (249 mg, 0.68 mmol) and 5a (130 mg, 1.08 mmol) as a white solid (152 mg, 49%) in a manner similar to that described in Example 36. $^1$H NMR (400 MHz, CDCl$_3$) δ 7.45 (d, 1H), 7.30-7.28 (m, 3H), 7.21 (d, 2H), 7.04 (d, 2H), 3.48 (s, 3H), 1.36 (s, 6H); ESMS m/z: 447.0 (M+1)

Example 45

Synthesis of 2-[5-(4-chloro-phenyl)-1-(2,4-dichloro-phenyl)-4-ethyl-1H-pyrazol-3-yl]-1,5,5-trimethyl-1,5-dihydro-imidazol-4-one (15)

Compound 15 was synthesized from 4c (252 mg, 0.63 mmol) and 5a (130 mg, 1.08 mmol) as a white solid (160 mg, 53%) in a manner similar to that described in Example 36. $^1$H NMR (400 MHz, CDCl$_3$) δ 7.46 (d, 1H), 7.31 (d, 2H), 7.28 (dd, 1H), 7.20 (d, 1H), 7.10 (d, 2H), 3.46 (s, 3H), 2.88 (q, 2H), 1.44 (s, 6H), 1.12 (t, 3H); ESMS m/z: 475.0 (M+1).

Example 46

Synthesis of 2-[5-(4-bromo-phenyl)-1-(2,4-dichloro-phenyl)-4-methyl-1H-pyrazol-3-yl]-1,5,5-trimethyl-1,5-dihydro-imidazol-4-one (16)

Compound 16 was synthesized from 4d (251 mg, 0.59 mmol) and 5a (130 mg, 1.08 mmol) as a white solid (170 mg, 57%) in a manner similar to that described in Example 36. $^1$H NMR (400 MHz, CDCl$_3$) δ 7.48~7.43 (m, 3H), 7.29 (dd, 1H), 7.19 (d, 1H), 7.01 (d, 2H), 3.49 (s, 3H), 2.41 (s, 3H), 1.43 (s, 6H); ESMS m/z: 505.0 (M+1).

Example 47

Synthesis of 2-[5-(4-bromo-phenyl)-1-(2,4-dichloro-phenyl)-4-ethyl-1H-pyrazol-3-yl]-1,5,5-trimethyl-1,5-dihydro-imidazol-4-one (17)

Compound 17 was synthesized from 4e (250 mg, 0.57 mmol) and 5a (130 mg, 1.08 mmol) as a white solid (160 mg, 54%) in a manner similar to that described in Example 36. $^1$H NMR (400 MHz, CDCl$_3$) δ 7.46~7.43 (m, 3H), 7.27 (dd, 1H), 7.20 (d, 1H), 7.01 (d, 2H), 3.44 (s, 3H), 2.84 (q, 2H), 1.41 (s, 6H), 1.09 (t, 3H); ESMS m/z: 519.1 (M+1).

Example 48

Synthesis of 2-[1-(2,4-dichloro-phenyl)-5-(4-methoxy-phenyl)-4-methyl-1H-pyrazol-3-yl]-1,5,5-trimethyl-1,5-dihydro-imidazol-4-one (18)

Compound 18 was synthesized from 4f (249 mg, 0.66 mmol) and 5a (130 mg, 1.08 mmol) as a white solid (143 mg, 46%) in a manner similar to that described in Example 36. $^1$H NMR (400 MHz, CDCl$_3$) δ 7.47 (d, 1H), 7.25 (dd, 1H), 7.16 (d, 1H), 7.06 (d, 2H), 6.84 (d, 2H), 3.79 (s, 3H), 3.49 (s, 3H), 2.40 (s, 3H), 1.43 (s, 6H); ESMS m/z: 457.0 (M+1).

Example 49

Synthesis of 2-[1-(2,4-dichloro-phenyl)-5-(4-fluoro-phenyl)-4-methyl-1H-pyrazol-3-yl]-1,5,5-trimethyl-1,5-dihydro-imidazol-4-one (19)

Compound 19 was synthesized from 4g (248 mg, 0.68 mmol) and 5a (130 mg, 1.08 mmol) as a white solid (121 mg, 39%) in a manner similar to that described in Example 36. $^1$H NMR (400 MHz, CDCl$_3$) δ 7.39 (d, 1H), 7.20 (dd, 1H), 7.13

(d, 1H), 7.06 (dd, 2H), 6.97 (dd, 2H), 3.43 (s, 3H), 2.33 (s, 3H), 1.36 (s, 6H); ESMS m/z: 445.0 (M+1).

Example 50

Synthesis of 2-[1-(2,4-dichloro-phenyl)-4-methyl-5-(4-trifluoromethyl-phenyl)-1H-pyrazol-3-yl]-1,5,5-trimethyl-1,5-dihydro-imidazol-4-one (20)

Compound 20 was synthesized from 4h (251 mg, 0.60 mmol) and 5a (130 mg, 1.08 mmol) as a white solid (176 mg, 60%) in a manner similar to that described in Example 36. $^1$H NMR (400 MHz, CDCl$_3$) δ 7.59 (d, 2H), 7.46 (d, 1H), 7.28 (m, 3H), 7.22 (d, 1H), 3.49 (s, 3H), 2.42 (s, 3H), 1.42 (s, 6H); ESMS m/z: 495.1 (M+1).

Example 51

Synthesis of 2-[5-(4-chloro-phenyl)-1-(2,4-dichloro-phenyl)-4-methyl-1H-pyrazol-3-yl]-1,5,5-trimethyl-1,5-dihydro-imidazole-4-thione (21)

To a solution of compound 6 (98 mg, 0.22 mmol) in toluene (5 mL) was added Lawesson's reagent (150 mg, 0.37 mmol) in one portion. The resulting mixture was heated at 60° C. for 4 h, then poured into ice water. The resulting mixture was extracted with ethyl acetate (2×30 mL). The combined extracts were washed with water, saturated aqueous sodium bicarbonate, and brine, dried over anhydrous sodium sulfate, filtered, and concentrated. The residue was purified by flash chromatography on silica gel with hexanes/ethyl acetate (7:3) to give the desired thioketone 21 (78 mg, 77%) as a yellow solid. $^1$H NMR (400 MHz, CDCl$_3$) δ 7.48 (d, 1H), 7.32 (d, 2H), 7.28 (dd, 1H), 7.22 (d, 1H), 7.08 (d, 2H), 3.62 (s, 3H), 2.48 (s, 3H), 1.55 (s, 6H); ESMS m/z: 477.0 (M+1).

Example 52

Synthesis of 2-[5-(4-chloro-phenyl)-1-(2,4-dichloro-phenyl)-4-ethyl-1H-pyrazol-3-yl]-1,5,5-trimethyl-1,5-dihydro-imidazol-4-thione (22)

Compound 22 was synthesized from 15 (100 mg, 0.21 mmol) as a yellow solid (62 mg, 58%) in a manner similar to that described in Example 51. $^1$H NMR (400 MHz, CDCl$_3$) δ 7.43 (d, 1H), 7.31 (d, 2H), 7.26 (dd, 1H), 7.21 (d, 1H), 7.09 (d, 2H), 3.58 (s, 3H), 2.91 (q, 2H), 1.51 (s, 6H), 1.09 (t, 3H); ESMS m/z: 491.0 (M+1).

Example 53

Synthesis of 2-[5-(4-chloro-phenyl)-1-(2,4-dichloro-phenyl)-4-methyl-1H-pyrazol-3-yl]-5,5-dimethyl-3,5-dihydro-imidazol-4-one (23)

To a solution of 4a (1.01 g, 2.62 mmol) in toluene (30 mL) at 0° C. were sequentially added DMF (0.2 mL) and oxalyl chloride (1.48 g, 11.66 mmol) dropwise. The mixture was allowed to warm to room temperature and stirred for 2 h, then transferred slowly to a mixture of 5i (0.56 g, 4.07 mmol) and triethylamine (0.42 g, 4.20 mmol) in THF (120 mL) at 0° C. After the mixture was warmed and stirred at room temperature for 15 h, water was added and the resulting mixture was extracted with ethyl acetate (2×30 mL). The combined extracts were washed with brine, dried over anhydrous sodium sulfate, filtered, and concentrated. The crude amide (1.02 g) thus obtained was treated with a solution of POCl$_3$ (1.25 g, 8.15 mmol) in dichloromethane (25 mL) at 80° C. for 4 h. The mixture was concentrated and poured into ice water. The resulting mixture was extracted with ethyl acetate (2×50 mL). The combined extracts were washed with brine, dried over anhydrous sodium sulfate, filtered, and concentrated. Purification of the residue by flash chromatography on silica gel with ethyl acetate/hexanes (7:3) afforded 23 (0.62 g, 53%) as a white solid. $^1$H NMR (400 MHz, CDCl$_3$) δ 7.43 (br s, 1H), 7.32~7.27 (m, 4H), 7.05 (d, 2H), 7.00 (br s, 1H), 2.38 (s, 3H), 1.81 (s, 6H); ESMS m/z: 447.0 (M+1).

Example 54

Synthesis of 2-[5-(4-chloro-phenyl)-1-(2,4-dichloro-phenyl)-4-ethyl-1H-pyrazol-3-yl]-5,5-dimethyl-3,5-dihydro-imidazol-4-one (24)

Compound 24 was synthesized from 4c (1.0 g, 2.53 mmol) and 5i (0.56 g, 4.07 mmol) as a white solid (0.58 g, 50%) in a manner similar to that described in Example 53. $^1$H NMR (400 MHz, CDCl$_3$) δ 7.43 (d, 1H), 7.30 (d, 2H), 7.30~7.27 (m, 2H), 7.07 (d, 2H), 7.00 (br s, 1H), 2.78 (q, 2H), 1.81 (s, 6H), 1.20 (t, 3H); ESMS m/z: 461.0 (M+1).

Example 55

Synthesis of 2-[5-(4-chloro-phenyl)-1-(2,4-dichloro-phenyl)-4-methyl-1H-pyrazol-3-yl]-1,3-diaza-spiro[4.4]non-1-en-4-one (25)

Compound 25 was synthesized from 4a (251 mg, 0.66 mmol) and 5j (140 mg, 0.98 mmol) as a white solid (140 mg, 45%) in a manner similar to that described in Example 53. $^1$H NMR (400 MHz, CDCl$_3$) δ 7.40 (d, 1H), 7.32~7.26 (m, 3H), 7.12 (s, 1H), 7.02 (d, 2H), 2.49 (m, 2H), 2.36 (s, 3H), 2.17 (m, 2H), 1.86 (m, 4H); ESMS m/z: 473.1 (M+1).

Example 56

Synthesis of 2-[5-(4-chloro-phenyl)-1-(2,4-dichloro-phenyl)-4-ethyl-1H-pyrazol-3-yl]-3,5-dihydro-imidazol-4-one (26)

Compound 26 was synthesized from 4c (1.0 g, 2.53 mmol) and 2-amino-acetamide hydrochloride (5k) (0.56 g, 4.56 mmol) as a white solid (0.81 g, 73%) in a manner similar to that described in Example 53. $^1$H NMR (400 MHz, CDCl$_3$) δ 7.43 (d, 1H), 7.31 (d, 2H), 7.30~7.27 (m, 2H), 7.07 (d, 2H), 4.35 (d, 2H), 2.77 (q, 2H), 1.20 (t, 3H); ESMS m/z: 433.1 (M+1).

Example 57

Synthesis of 2-[5-(4-chloro-phenyl)-1-(2,4-dichloro-phenyl)-4-methyl-1H-pyrazol-3-yl]-3,5,5-trimethyl-3,5-dihydro-imidazol-4-one (27)

To a solution of sodium hydride (14.4 mg, 0.66 mole) in DMF (3 mL) at 0° C. was added compound 23 (100 mg, 0.22 mmol) in one portion. The mixture was allowed to warm to room temperature and stirred for 30 min, at which time methyl iodide (2 g, 14.08 mmol) was added. After the mixture was stirred for 2 h, water was added and the resulting mixture was extracted with ethyl acetate (2×50 mL). The combined extracts were washed with brine, dried over anhydrous sodium sulfate, filtered, and concentrated. Purification of the crude residue by flash chromatography on silica gel with hexanes/ethyl acetate (1:1) gave the product 27 (70 mg, 0.15 mmol, 68%) as a white solid. $^1$H NMR (400 MHz, CDCl$_3$) δ 7.45 (d, 1H), 7.30 (d, 2H), 7.26 (dd, 1H), 7.18 (d, 1H), 7.07 (d, 2H), 3.28 (s, 3H), 2.24 (s, 3H), 1.87 (s, 6H); ESMS m/: 461.1 (M+1).

Example 58

Synthesis of 2-[5-(4-chloro-phenyl)-1-(2,4-dichloro-phenyl)-4-ethyl-1H-pyrazol-3-yl]-3,5,5-trimethyl-3,5-dihydro-imidazol-4-one (28)

Compound 28 was synthesized from compound 24 (101 mg, 0.22 mmol) and methyl iodide (2 g, 14.08 mmol) as a white solid (70 mg, 68%) in a manner similar to that described in Example 57. $^1$H NMR (400 MHz, CDCl$_3$) δ 7.42 (br s, 1H), 7.29 (d, 2H), 7.24 (d, 1H), 7.19 (d, 1H), 7.07 (d, 2H), 3.21 (s, 3H), 2.62 (q, 2H), 1.85 (s, 6H), 1.11 (t, 3H); ESMS m/z: 475.1 (M+1).

Example 59

Synthesis of 2-[5-(4-chloro-phenyl)-1-(2,4-dichloro-phenyl)-4-ethyl-1H-pyrazol-3-yl]-3-methyl-3,5-dihydro-imidazol-4-one (29)

To a solution of 26 (100 mg, 0.23 mmol) in acetonitrile (8 mL) at room temperature was sequentially added potassium carbonate (150 mg, 1.09 mole) and methyl iodide (2 g, 14.08 mmol) slowly. The mixture was stirred at 60° C. for 6 h. Water was added and the resulting mixture was extracted with ethyl acetate (2×50 mL). The combined extracts were washed with brine, dried over anhydrous sodium sulfate, filtered, and concentrated. Purification of the crude residue by flash chromatography on silica gel eluting with hexanes/ethyl acetate (1:1) gave the compound 29 (70 mg, 68%) as a white solid. $^1$H NMR (400 MHz, CDCl$_3$) δ 7.45 (d, 1H), 7.30 (d, 2H), 7.25 (dd, 1H), 7.18 (d, 1H), 7.09 (d, 2H), 4.88 (s, 0.82H), 4.51 (s, 1.18H), 3.42 (s, 1.77H), 3.24 (s, 1.23H), 2.65 (q, 2H), 1.15 (t, 3H); ESMS m/: 447.0 (M+1).

Example 60

Synthesis of 3-butyl-2-[5-(4-chloro-phenyl)-1-(2,4-dichloro-phenyl)-4-ethyl-1H-pyrazol-3-yl]-3,5-dihydro-imidazol-4-one (30)

Compound 30 was synthesized from 26 (102 mg, 0.23 mmol) and n-butyl bromide (500 mg, 3.65 mmol) as a white solid (55 mg, 49%) in a manner similar to that described in Example 59. $^1$H NMR (400 MHz, CDCl$_3$) δ 7.44 (d, 1H), 7.30 (d, 2H), 7.25 (dd, 1H), 7.17 (d, 1H), 7.09 (d, 2H), 4.83 (s, 0.82H), 4.45 (s, 1.18H), 3.80 (s, 1.18H), 3.67 (s, 0.82H), 2.65 (q, 2H), 1.69 (br s, 2H), 1.42-1.25 (m, 2H), 1.13 (t, 3H), 0.97-0.86 (m, 3H); ESMS m/: 489.1 (M+1).

Example 61

Synthesis of 2-[5-(5-bromo-thiophen-2-yl)-1-(2,4-dichloro-phenyl)-4-methyl-1H-pyrazol-3-yl]-1,5,5-trimethyl-1,5-dihydro-imidazol-4-one (33)

Compound 33 was synthesized from 31a (251 mg, 0.58 mmol) and 5a (130 mg, 1.08 mmol) as a white solid (152 mg, 51%) in a manner similar to that described in Example 36. $^1$H NMR (400 MHz, CDCl$_3$) δ 7.53 (d, 1H), 7.36 (dd, 1H), 7.26 (d, 1H), 6.96 (d, 1H), 6.67 (d, 1H), 3.45 (s, 3H), 2.49 (s, 3H), 1.42 (s, 6H); ESMS m/z: 511.0 (M+1).

Example 62

Synthesis of 2-[5-(5-bromo-thiophen-2-yl)-1-(2,4-dichloro-phenyl)-4-ethyl-1H-pyrazol-3-yl]-1,5,5-trimethyl-1,5-dihydro-imidazol-4-one (34)

Compound 34 was synthesized from 31b (248 mg, 0.56 mmol) and 5a (130 mg, 1.08 mmol) as a white solid (149 mg, 51%) in a manner similar to that described in Example 36. $^1$H NMR (400 MHz, CDCl$_3$) δ 7.46 (d, 1H), 7.32 (dd, 1H), 7.25 (d, 1H), 6.91 (d, 1H), 6.62 (d, 1H), 3.40 (s, 3H), 2.90 (q, 2H), 1.37 (s, 6H), 1.14 (t, 3H); ESMS m/z: 525.0 (M+1).

Example 63

Synthesis of 2-[1-(2,4-dichloro-phenyl)-4-methyl-5-(5-pent-1-ynyl-thiophen-2-yl)-1H-pyrazol-3-yl]-1,5,5-trimethyl-1,5-dihydro-imidazol-4-one (35)

Compound 35 was synthesized from 31c (251 mg, 0.60 mmol) and 5a (130 mg, 1.08 mmol) as a white solid (151 mg, 50%) in a manner similar to that described in Example 36. $^1$H NMR (400 MHz, CDCl$_3$) δ 7.52 (d, 1H), 7.36 (dd, 1H), 7.27 (d, 1H), 6.97 (d, 1H), 6.73 (d, 1H), 3.46 (m, 5H), 2.52 (m, 5H), 1.42 (s, 6H), 1.00 (t, 3H); ESMS m/z: 499.0 (M+1).

Example 64

Synthesis of 2-{1-(2,4-dichloro-phenyl)-4-methyl-5-[5-(4-methyl-pent-1-ynyl)-thiophen-2-yl]-1H-pyrazol-3-yl}-1,5,5-trimethyl-1,5-dihydro-imidazol-4-one (36)

Compound 36 was synthesized from 31d (250 mg, 0.58 mmol) and 5a (130 mg, 1.08 mmol) as a white solid (172 mg, 57%) in a manner similar to that described in Example 36. $^1$H NMR (400 MHz, CDCl$_3$) δ 7.50 (d, 1H), 7.33 (dd, 1H), 7.26 (d, 1H), 6.96 (d, 1H), 6.70 (d, 1H), 3.43 (s, 3H), 2.47 (s, 3H), 2.26 (d, 2H), 1.85 (m, 1H), 1.39 (s, 6H), 0.97 (d, 6H); ESMS m/z: 513.0 (M+1).

Example 65

Synthesis of 2-{1-(2,4-dichloro-phenyl)-4-ethyl-5-[5-(4-methyl-pent-1-ynyl)-thiophen-2-yl]-1H-pyrazol-3-yl}-1,5,5-trimethyl-1,5-dihydro-imidazol-4-one (37)

Compound 37 was synthesized from 31e (250 mg, 0.56 mmol) and 5a (130 mg, 1.08 mmol) as a white solid (142 mg, 47%) in a manner similar to that described in Example 36. $^1$H NMR (400 MHz, CDCl$_3$) δ 7.44 (d, 1H), 7.25 (dd, 1H), 7.20 (d, 1H), 6.90 (d, 1H), 6.65 (d, 1H), 3.37 (s, 3H), 2.90 (q, 2H), 2.23 (d, 2H), 1.82 (m, 1H), 1.35 (s, 6H), 1.12 (t, 3H), 0.94 (d, 6H); ESMS m/z: 527.0 (M+1).

Example 66

Synthesis of 2-{1-(2,4-dichloro-phenyl)-5-[5-(3,3-dimethyl-but-1-ynyl)-thiophen-2-yl]-4-methyl-1H-pyrazol-3-yl}-1,5,5-trimethyl-1,5-dihydro-imidazol-4-one (38)

Compound 38 was synthesized from 31f (251 mg, 0.58 mmol) and 5a (130 mg, 1.08 mmol) as a white solid (182 mg, 61%) in a manner similar to that described in Example 36. $^1$H NMR (400 MHz, CDCl$_3$) δ 7.47 (d, 1H), 7.31 (dd, 1H), 7.24 (d, 1H), 6.92 (d, 1H), 6.66 (d, 1H), 3.41 (s, 3H), 2.45 (s, 3H), 1.37 (s, 6H), 1.23 (s, 9H); ESMS m/z: 513.0 (M+1).

Example 67

Synthesis of 2-{1-(2,4-dichloro-phenyl)-4-ethyl-5-[5-(4-phenyl-but-1-ynyl)-thiophen-2-yl]-1H-pyrazol-3-yl}-1,5,5-trimethyl-1,5-dihydro-imidazol-4-one (39)

Compound 39 was synthesized from 31g (251 mg, 0.50 mmol) and 5a (130 mg, 1.08 mmol) as a white solid (145 mg, 49%) in a manner similar to that described in Example 36. $^1$H NMR (400 MHz, CDCl$_3$) δ 7.46 (d, 1H), 7.41 (m, 4H), 7.20 (m, 3H), 6.93 (d, 1H), 6.67 (d, 1H), 3.45 (s, 3H), 2.88 (t, 2H), 2.67 (m, 4H), 1.56 (s, 6H), 1.14 (t, 3H); ESMS m/z: 575.0 (M+1).

Example 68

Synthesis of 2-[5-(5-Bromo-thiophen-2-yl)-1-(2,4-dichloro-phenyl)-4-ethyl-1H-pyrazol-3-yl]-1,5,5-trimethyl-1,5-dihydro-imidazole-4-thione (40)

Compound 40 was synthesized from 34 (90 mg, 0.17 mmol) as a yellow solid (68 mg, 73%) in a manner similar to that described in Example 51. $^1$H NMR (400 MHz, CDCl$_3$) δ 7.49 (d, 1H), 7.33 (m, 2H), 6.94 (d, 1H), 6.66 (d, 1H), 3.55 (s, 3H), 2.98 (q, 2H), 1.50 (s, 6H), 1.17 (t, 3H); ESMS m/z: 541.0 (M+1).

Example 69

Synthesis of 2-{1-(2,4-dichloro-phenyl)-4-methyl-5-[5-(4-methyl-pent-1-ynyl)-thiophen-2-yl]-1H-pyrazol-3-yl}-1,5,5-trimethyl-1,5-dihydro-imidazole-4-thione (41)

Compound 41 was synthesized from 36 (110 mg, 0.21 mmol) as a yellow solid (72 mg, 62%) in a manner similar to that described in Example 51. $^1$H NMR (400 MHz, CDCl$_3$) δ 7.52 (d, 1H), 7.36 (dd, 1H), 7.28 (d, 1H), 6.98 (d, 1H), 6.73 (d, 1H), 3.58 (s, 3H), 2.60 (s, 3H), 2.28 (d, 2H), 1.85 (m, 1H), 1.52 (s, 6H), 0.98 (d, 6H); ESMS m/z: 529.1 (M+1).

Example 70

Synthesis of 2-{1-(2,4-dichloro-phenyl)-4-ethyl-5-[5-(4-methyl-pent-1-ynyl)-thiophen-2-yl]-1H-pyrazol-3-yl}-1,5,5-trimethyl-1,5-dihydro-imidazole-4-thione (42)

Compound 42 was synthesized from 37 (93 mg, 0.18 mmol) as a yellow solid (60 mg, 63%) in a manner similar to that described in Example 51. $^1$H NMR (400 MHz, CDCl$_3$) δ 7.50 (d, 1H), 7.32 (m, 2H), 6.97 (d, 1H), 6.72 (d, 1H), 3.77 (s, 3H), 3.02 (q, 2H), 2.28 (d, 2H), 1.87 (m, 1H), 1.53 (s, 6H), 1.19 (t, 3H), 0.99 (d, 6H); ESMS m/z: 543.1 (M+1).

Example 71

Synthesis of 2-[1-(2,4-dichloro-phenyl)-4-methyl-5-(5-pent-1-enyl-thiophen-2-yl)-1H-pyrazol-3-yl]-1,5,5-trimethyl-1,5-dihydro-imidazol-4-one (43)

Compound 43 was synthesized from 32 (0.61 g, 1.42 mmol) and 5a (0.30 g, 2.58 mmol) as a white solid (0.51 g, 70%) in a manner similar to that described in Example 36. $^1$H NMR (400 MHz, CDCl$_3$) δ 7.48 (d, 1H), 7.31 (dd, 1H), 7.27 (d, 1H), 6.70 (d, 1H), 6.65 (d, 1H), 6.38 (d, 1H), 5.98 (dd, 1H), 3.43 (s, 3H), 2.47 (s, 3H), 2.11 (m, 2H), 1.46 (m, 2H), 1.38 (s, 6H), 0.90 (t, 3H); ESMS m/z: 501.0 (M+1).

Example 72

Synthesis of 2-[1-(2,4-dichloro-phenyl)-4-methyl-5-(5-pentyl-thiophen-2-yl)-1H-pyrazol-3-yl]-1,5,5-trimethyl-1,5-dihydro-imidazol-4-one (44)

A mixture of 43 (118 mg, 0.24 mmol) and Pd—C (12 mg) in MeOH (8 mL) was stirred under 1 atm of H$_2$ at room temperature for 2 h. The reaction mixture was filtered and the resulting filtrate was concentrated under reduced pressure to give the crude residue, which was subjected to purification by flash chromatography on silica gel with hexanes/ethyl acetate (1:1) to afford the product 44 (75 mg, 62%) as a white solid. $^1$H NMR (400 MHz, CDCl$_3$) δ 7.48 (d, 1H), 7.29 (m, 2H), 6.77 (d, 1H), 6.61 (d, 1H), 3.57 (s, 3H), 2.65 (m, 5H), 1.60 (m, 8H), 1.22 (m, 4H), 0.81 (t, 3H); ESMS m/z: 503.0 (M+1).

Example 73

Radioligand Binding Assay

Human CB1 and CB2 receptors were obtained from HEK293 cell lines stably expressing CB1 and CB2 receptors. Briefly, cells expressing a CB1 or CB2 receptor were harvested and subjected to sonication. The lyzed cells were centrifuged for 30 minutes at 43,000×g at 4° C. The resultant pellets were re-suspended in a buffer (50 mM Tris, 5 mM MgCl$_2$, 2.5 mM EDTA, pH 7.4, 10% sucrose) and stored at −80° C. The protein concentration of the purified membrane was determined by the Bradford method as described in the manual provided by Bio-Rad Laboratories, Inc. (Hercules, Calif.).

The affinity of towards CB1 and CB2 receptor was determined by an in vitro radioligand binding assay as follows. 0.2~8 μg of membrane fractions prepared from CB1 or CB2-expressing cell lines described above were mixed with a buffer (pH 7.4, 50 mM Tris-HCl, 5 mM MgCl$_2$, 1 mM EDTA, and 0.3% BSA) containing 0.75 nM [$^3$H]CP55,940 (a ligand that specifically binds to CB1 and CB2 receptors) and a test compound. Non-radioactive CP55,940 (1 μM) was used instead of the test compound in a control assay. The mixture was incubated for 1.5 hours at 30° C. in Multiscreen microplates (Millipore, Billerica, Mass.) to allow the test compound or [$^3$H]CP55,940 to bind to the receptor. The binding reaction was terminated by Manifold filtration, in which the membrane fractions (containing a CB1 or CB2 receptor) were retained on the filters. The filters were then washed with an ice-cold wash buffer (50 mM Tris, pH 7.4, 0.25% BSA) four times to remove free [$^3$H]CP55,940. The radioactivity of the membrane fractions bound to the filters was measured by Topcount (Perkin Elmer Inc.). IC$_{50}$ (the concentration of the test compound required to inhibit 50% of the binding of [$^3$H]CP55,940 to the receptor) were calculated.

Compounds 6-30 and 33-44 were tested in this assay. Unexpectedly, all of the test compounds have IC$_{50}$ values between 1 nM and 10 μM for inhibiting binding of [$^3$H]CP55,940 towards CB1 and CB2 receptors, respectively.

Example 74

DELFIA GTP-Binding Kit Assay

The activity of a test compound in modulating CB1 receptor was determined by the method described in the following paragraph using the DELFIA GTP-binding kit supplied by PerkinElmer Inc. (Boston, Mass.). The DELFIA GTP-binding assay is a time-resolved fluorometric assay based on GDP-GTP exchange on G-protein subunits after activation of a G protein-coupled receptor. Note that stimulation of a CB1 receptor by CP55,940 results in replacement of GDP by GTP on the α-subunit of G-protein, leading to GTP-Gα complex, i.e., the activated form of G-protein. Eu-GTP, a non-hydrolysable GTP labeled with the Europium chelate, is used to monitor agonist-dependent activation of G-protein. See Peltonen et al., Eur. J. Pharmacol. (1998) 355:275.

Plasma membrane derived from HEK293 cells expressing human CB1 receptor was suspended in an assay buffer (50 mM HEPES, pH 7.4, 100 mM NaCl, 100 μg/mL saponin, 5 mM $MgCl_2$, 2 μM GDP, 0.5% BSA). An aliquot of the membrane was added to each well of AcroPlate (Pall Life Sciences, Ann Arbor, Mich.) together with a test compound (various concentrations in 0.1% DMSO) and CP55,940 (20 nM in the assay buffer). The assay plate was incubated in dark at 30° C. for 60 minutes. Eu-GTP was then added to each well and the plate was incubated for another 30 minutes at 30° C. in dark. The plate was washed four times with a wash solution provided in the assay kit. Binding of Eu-GTP was detected based on the fluorescence signal determined by a Victor 2 multi-label reader. The $EC_{50}$ value (i.e., 50% inhibition of CP55,940-stimulating Eu-GTP binding) for each test compound was determined by a concentration-response curve using nonlinear regression (Prism; GraphPad, San Diego, Calif.).

Compounds 6-30 and 33-44 were tested in this assay. Unexpectedly, all of the test compounds have $EC_{50}$ values between 1 nM and 10 μM for inhibiting Eu-GTP binding by modulating CP55,940-stimulating CB1 receptor activation.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

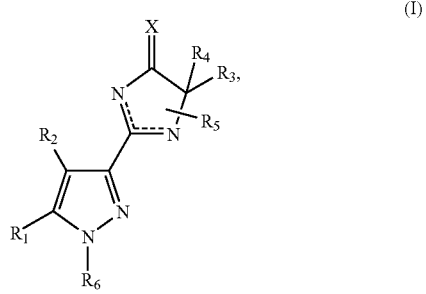

(I)

wherein
one of the two ---- bonds is a single bond and the other is a double bond;
X is O or S; and
each of $R_1$ and $R_6$, independently, is aryl, heteroaryl, cycloalkyl, cycloalkenyl, heterocycloalkyl, or heterocycloalkenyl;

each of $R_2$, $R_3$, $R_4$, and $R_5$, independently, is H, halo, alkyl, alkenyl, alkynyl, aryl, heteroaryl, cycloalkyl, cycloalkenyl, heterocycloalkyl, or heterocycloalkenyl, or $R_3$ and $R_4$, together with the carbon atom to which they are bonded, are cycloalkyl, cycloalkenyl, heterocycloalkyl, heterocycloalkenyl, aryl, or heteroaryl.

2. The compound of claim 1, wherein X is O.

3. The compound of claim 2, wherein $R_6$ is aryl or heteroaryl.

4. The compound of claim 3, wherein $R_6$ is phenyl substituted with halo.

5. The compound of claim 4, wherein $R_1$ is aryl or heteroaryl.

6. The compound of claim 5, wherein $R_1$ is phenyl or thiophenyl.

7. The compound of claim 6, wherein each of $R_2$, $R_3$, $R_4$, and $R_5$, independently, is H or alkyl.

8. The compound of claim 2, wherein $R_1$ is aryl or heteroaryl.

9. The compound of claim 8, wherein $R_1$ is phenyl or thiophenyl.

10. The compound of claim 9, wherein each of $R_2$, $R_3$, $R_4$, and $R_5$, independently, is H or alkyl.

11. The compound of claim 2, wherein each of $R_2$, $R_3$, $R_4$, and $R_5$, independently, is H or alkyl.

12. The compound of claim 1, wherein X is S.

13. The compound of claim 12, wherein $R_6$ is aryl or heteroaryl.

14. The compound of claim 13, wherein $R_6$ is phenyl substituted with halo.

15. The compound of claim 14, wherein $R_1$ is aryl or heteroaryl.

16. The compound of claim 15, wherein $R_1$ is phenyl or thiophenyl.

17. The compound of claim 16, wherein each of $R_2$, $R_3$, $R_4$, and $R_5$, independently, is H or alkyl.

18. The compound of claim 12, wherein $R_1$ is aryl or heteroaryl.

19. The compound of claim 18, wherein $R_1$ is phenyl or thiophenyl.

20. The compound of claim 19, wherein each of $R_2$, $R_3$, $R_4$, and $R_5$, independently, is H or alkyl.

21. The compound of claim 12, wherein each of $R_2$, $R_3$, $R_4$, and $R_5$, independently, is H or alkyl.

22. A pharmaceutical composition, comprising a compound of claim 1 and a pharmaceutically acceptable carrier.

23. The composition of claim 22, wherein $R_6$ is aryl or heteroaryl.

24. The composition of claim 23, wherein $R_6$ is aryl substituted with halo.

25. The composition of claim 24, wherein $R_1$ is aryl or heteroaryl.

26. The composition of claim 25, wherein $R_1$ is phenyl or thiophenyl.

27. The composition of claim 26, wherein each of $R_2$, $R_3$, $R_4$, and $R_5$, independently, is H or alkyl.

28. The composition of claim 22, wherein $R_1$ is aryl or heteroaryl.

29. The composition of claim 28, wherein $R_1$ is phenyl or thiophenyl.

30. The composition of claim 29, wherein each of $R_2$, $R_3$, $R_4$, and $R_5$, independently, is H or alkyl.

31. The composition of claim 22, wherein each of $R_2$, $R_3$, $R_4$, and $R_5$, independently, is H or alkyl.

* * * * *